US008030047B2

(12) United States Patent
Romette et al.

(10) Patent No.: US 8,030,047 B2
(45) Date of Patent: Oct. 4, 2011

(54) ACTIVE TRUNCATED FORM OF THE RNA POLYMERASE OF *FLAVIVIRUS*

(75) Inventors: **Jean-Lou

FIG. 1A

```
                           A1            A2            B1        A3                        αx
            1         10           20          30          40           50          60
            .         .            .           .           .            .           .
Seq.ID.  1 Dengue2                  .GTGNIGETLGEKWKSRLNALGKSEFQIYKKSGIQEVDRTLAKEGIKRG.ETDHHAVSRGSAKLRWFVERN
Seq.ID.  2 Dengue3                  .GTGSQGETLGEKWKEKLENQLSRKEDLYKKSGITEVDRTEAKEGLKRG.EITHHAVSRGSAKLQWFVBRN
Seq.ID.  3 Dengue1                  .GTGAQGETLGEKWKEKQLENQLSKSEFNTYKRSGIMEVDRSEAKEGLKRG.ETTKHAVSRGSKIRWIVERG
Seq.ID.  4 Dengue4                  .GTGTTGETLGEKWKEREEYKRSGILEVDRTEAKSALKDG.SKIKHAVSRGSSKTAKLRWLVERR
Seq.ID.  5 WestNile                 ..GGAKGRTLGEVWKERENQMTKEEFTRYRKEAIIEVDRSAAKHARKEGNVTGGHSVSRGTAKLRWLVERR
Seq.ID.  6 Kunjin                   ..GGAKGRTLGEVWKERENQMTKEEFIRYRKEAIIEVDRSAAKHARKERNITGGHPVSRGTAKLRWLVERR
Seq.ID.  7 JapaneseEncephalitis     ..GRPGGRTLGEQWKEKNAMSREEFFKYRREAIIEVDRTEAARRENNIVGGHPVSRGSAKLRWLVEKG
Seq.ID.  8 YellowFever              .GTANGKTLGEVWKEREELLLDKQQFELYKRTDIVEVDRDTARRHLAEGKVDTGVAVSRGTAKLRWFHERG
Seq.ID.  9 Banzi                    .GGSSALTYGEVWKERENLLGKQENLGKQEMNYKVSDILEVDRSHAREVLNSGNDAVGVAVSRGSSKLNWLIERG
Seq.ID. 10 Langat                   .GGSEGDTLGDMKKARLNSCTKEEFFAYRRAGVMETDREKARELLKRGETNMGLAVSRGTSKLAWMEERG
Seq.ID. 11 Powassan                 .GGAEGSTLGDIWKERRLNSCTKEEFFAYRRTGVMETNRDQARELLRRGETNMGLAVSRGCAKLAWLEERG
Seq.ID. 12 Tick-borneEncephalitis   .GGSEGDTLGDLWKERRLNGCTKEEFFAYRRTGILETERDKARELLRRGETNMGLAVSRGTAKLAWLEERG
Seq.ID. 13 LoupingIll               ..GGSDGDTLGDLWKERRLNNCTKEEFFVYRRTGILETERDKARELLRRGETNMGLAVSRGTAKLAWLEERG
Seq.ID. 14 Modoc                    RGICSSAPTLGEIWKRKLNQLDAKEFMAYRRRFVVEVDRNEAREALAKGKTNTGHAVSRGTAKLAWIDERG
Seq.ID. 15 RioBravo                 RGVSSSYITYGEQWKRELNKLNAQABFLYKSRLVHEIDRAEAVSNLSKGRTNTGHAVSRGTSKLAWMHERG β1              αA                   β2              β3
            70          80           90          100          110          120         130
            .           .            .           .            .            .           .
Seq.ID.  1 Dengue2                  MVTPECKVVDLGCGRGGWSYYCGGLKNVREVKGLTKG.GPGHEEPIPMSTYGWNLVRLQSGVDVFFTPPEK
Seq.ID.  2 Dengue3                  MVIPECRVIDLGCGRGGWSYYCAGLKKVTEVRGYTKG.GPGHEEPVPMSTYGWNIVKLMSGKDVFYLPPEK
Seq.ID.  3 Dengue1                  LVKPECKVIDLGCGRGGWSYYCAGLKKVTEVKGYTKG.GPGHEEPIPMATYGWNLVKLHSGKDVFFTPPEK
Seq.ID.  4 Dengue4                  MVKPKGKVVDLGCGRGGWSYYMATLKNVTEVKGYTKG.GPGHEEPIPMATYGWNLVKLHSGVDVFYKPTEQ
Seq.ID.  5 WestNile                 FLEPVGKVIDLGCGRGGWCYYMATQKRVQEVRGYTKG.GPGHEEPQLVQSYGWNIVTMKSGVDVFYRPSEC
Seq.ID.  6 Kunjin                   FLEPVGKVIDLGCGRGGWCYYMATQKRVQEVRGYTKG.GPGHEEPQLVQSYGWNIVTMKSGVDVFYRPSEC
Seq.ID.  7 JapaneseEncephalitis     FVSPIGKVIDLGCGRGGWSYYAATLKKVQEVRGYTKG.GPGHEEPMLMQSYGWNLVSLKSGVDVFYKPSEP
Seq.ID.  8 YellowFever              YVKLEGRVIDLGCGRGGWSYYAAAAQKEVSGVKGFTLG.GAGHEEPMNVQSLGWNIITFKDKTDIHRLEPVK
Seq.ID.  9 Banzi                    YLRPTGRVVDLGCGRGGWSYVKGFTVCAAERQVTSVKAYTLG.RDGHEKSPRMVTSLGWNLIKFEKDKSDITRMTPHA
Seq.ID. 10 Langat                   YVTLKGEVVDLGCGRGGWSYYAASRPAVMSVRAYTLG.KGKHESPRMVTSLGWNLIKFRAGMDVFSMEPHR
Seq.ID. 11 Powassan                 YATLKGEVVDLGCGRGGWSYYAASRPSVMAVRAYTLG.GKGHEAPRLVTSLGWNLIKFRSGMDVFSMATTR
Seq.ID. 12 Tick-borneEncephalitis   YATLKGEVVDLGCGRGGWSYYAASRPAVMSVRAYTIG.GKGHETPKMVTSLGWNLIKFRAGVDVFSMQPHR
Seq.ID. 13 LoupingIll               YRTLKGEVVDLGCGRGGWSYYAASRPAVMSVRAYTIG.GRGHEVPKMVTSLGWNLIREFRSGMDVFSMQPHR
Seq.ID. 14 Modoc                    GVELKGSVVDLGCGRGGWSYYAASQPNVREVRKVKAYTLG.TSGHEKPRLVETFGWNLITEKSKVDVRKMEFFQ
Seq.ID. 15 RioBravo                 YVPLKGWVVDLGCGRGGWSYYAAAQERVRKVNAYTLATTKGHEQPRLVQSYGWNLVTFK.KADVRTIEPYP
```

FIG. 1B (Figure shows a multiple sequence alignment of 15 flavivirus sequences (Dengue2, Dengue3, Dengue1, Dengue4, WestNile, Kunjin, JapaneseEncephalitis, YellowFever, Banzi, Langat, Powassan, Tick-borneEncephalitis, LoupingIll, Modoc, RioBravo) across residues 140–270, with secondary structure elements β4, αD, β5, αE, β6, β7, A4, B2, B3 annotated, and regions labeled NS5MTase and NS5Pol.)

FIG. 1C

```
          280        290        300        310        320        330        340
           |          |          |          |          |          |          |
Seq.ID.  1 Dengue2            KRIEKIKQEHETSWHYDQDHPYKTWAYHGSYETKQTGSASSMGNGVRLLTKPWDVVPMVTQMAMTDTTPF
Seq.ID.  2 Dengue3            ERIKRIKEEHSSTWHYDENPYKTWAYHGSYEVKATGSASSMINGVKLLTKPWDVVPMVTQMAMTDTTPF
Seq.ID.  3 Dengue1            QRIENIKNEHKSTWHYDEDNPYKTWAYHGSYEVKPSGSASSMVNGVRLLTKPWDVIPMVTQIAMTDTTPF
Seq.ID.  4 Dengue4            RRLQRLQEEHKETWHYDQENPYRTWAYHGSYEAPSTGSASSMVYGVKLLTKPWDVIPMVTQLAMTDTTPF
Seq.ID.  5 WestNile           NRIERLRREYSSTWHHDENHPYRTWNYHGSYDVKPTGSASSLVNGVRLLSKPWDTITNVTTMAMTDTTPF
Seq.ID.  6 Kunjin             NRIERLRREYSSTWHHDENHPYRTWNYHGSYEVKPTGSASSLVNGVRLLSKPWDTITNVTTMAMTDTTPF
Seq.ID.  7 JapaneseEncephalitis KRIQKLKEEFATTWHKDPEHPYRTWTYHGSYEVKATGSASSLVNGVVKLMSKPWDAIANVTTMAMTDTTPF
Seq.ID.  8 YellowFever        ERVERIKSEYMTSWFYDNDNPYRTWHYCGSYVTKTSGSAASMVNGVIKILTYPWDKIEEVTRMAMTDTTPF
Seq.ID.  9 Banzi              ARINRLKEEQESTWFVDSDHPYRTWHYHGSYVAKQSGTAASMINGVVKLLSGPWDRIEEVTNMAMTDTTPF
Seq.ID. 10 Langat             ERIQALKDQYCDTWHEDHEHPYRTWQYWGSYKTAATGSSASLINGVVKLLSWPWNAREDVVRMAMTDTTAF
Seq.ID. 11 Powassan           ERIGALREQYSESWHEDKEHPYRTWQYWGSYRTPATGSAASLINGVVKLLSWPWNAREDVTRMAMTDTTAF
Seq.ID. 12 Tick-borneEncephalitis ERISALREQYGETWHMDREHPYRTWQYWGSYRTAPTGSAASLINGVVKLLSWPWNAREDVVRMAMTDTTAF
Seq.ID. 13 LoupingIll         ERIRALRKQYSETWHMDEEHPYRTWQYWGTSRTAPTGSAASLINGVVKLLSWPWNAREDVVRMAMTDTTAF
Seq.ID. 14 Modoc              MRVDKIKAEKSGTWCFDSNHPYRTWNYHGSYRVRDVGTRASAVNHVVKLLSWPWGRMEKVLAMSMTDTTAF
Seq.ID. 15 RioBravo           DRITIQNENKASWHQDPNQPYRTWTYHGSYSIRDVGTSASAPNHVVKLLAWPWLKIEKVVLMAMTDTTAF
```

ACTIVE TRUNCATED FORM OF THE RNA POLYMERASE OF *FLAVIVIRUS*

CROSS REFERENCE TO RELATED APPLICATION

This application is a divisional of U.S. application Ser. No. 10/857,244 filed May 28, 2004, pending, and claims the benefit of U.S. Provisional Application No. 60/474,670, filed May 30, 2003, the subject matter of which is fully incorporated herein by reference.

FIELD OF INVENTION

This invention relates to antiviral molecular biology. More particularly, it relates to the isolation and identification of an active truncated form of the RNA polymerase of *flavivirus*, capable of being easily reproduced, and serving as a target for high-throughput screening of antiviral drugs.

BACKGROUND

The genus *flavivirus* contains approximately 70 positive single-stranded RNA viruses, among which many major human pathogens are found, including Dengue virus ("DV"), West Nile ("WNV"), Yellow Fever virus ("YFV"), Japanese and tick-borne encephalitis viruses. YFV was the first *flavivirus* to be isolated in 1927, but historically, flavivirus-like diseases have been reported in the medical literature since at least 1780.

On of the most common and virulent *flaviviruses* is DV. DV threatens up to 2.5 billion people in 100 endemic countries. Up to 50 million infections occur annually with 500 000 cases of dengue haemorrhagic fever and 22,000 deaths mainly among children. Dengue has been classified by the World Health Organization ("WHO") as a priority as it ranks as the most important mosquito-borne viral disease in the world. In the last 50 years, its incidence has increased 30-fold. Prior to 1970, only 9 countries had experienced cases of dengue haemorrhagic fever ("DHF"); since then the number has increased more than 4-fold and continues to rise.

WNV also has become much more wide-spread. In 1999, WNV was isolated for the first time in the Americas during an outbreak in New York City. By the end of 2002, WNV activity had been identified in 44 states of the United States and the District of Columbia. The 2002 WNV epidemic resulted in 4,156 reported human cases of WN disease including 2,942 meningoencephalitis cases and 284 deaths.

There have been previous attempts to generate a vaccine. For example, a live, attenuated virus of YFV (strain 17D) was developed in 1936 and has been used as a vaccine for over 400 million people. Unfortunately, the vaccine has not proved 100% successful since there are 200,000 estimated cases of yellow fever (with 30,000 deaths) per year worldwide, 90% of which in Africa. Chimeric live vaccines incorporating genes of either Japanese encephalitis, WNV, or Dengue in a YFV 17D vector are currently in development. However, a number of difficulties are associated with the conception of safe and efficient vaccines, such as vaccine purity, and immunogenic cross responses. That is why antiviral chemotherapy has a major role to play in the control of such diseases.

Since viral RNA polymerase is critical for replication of the virus and cannot be substituted by any other cellular polymerase, it is an excellent antiviral target. As a result, most of the more than 30 new antiviral agents, which have been developed and approved during the last 5 years, are directed against viral polymerases. They are mainly targeted against human immuno-deficiency virus, but drugs against hepatitis B and C, herpes simplex, varicella-zoster and influenza virus infections have also been made commercially available.

More than 50% of these antiviral agents are nucleoside analogues, in which the base, the ribose moiety or both have been modified. Nucleoside analogues can act as inhibitory ligands by binding to the template binding site within the polymerase active site and preventing the access of the viral RNA, or by binding to the nucleotide binding site, thus limiting the availability of the natural substrate for complementary strand synthesis. It is generally understood in the art that a nucleoside analogue may be a synthetic molecule that resembles a naturally occurring nucleoside, but lacks a bond site needed to link it to an adjacent nucleotide. Additionally, nucleoside analogues can also act as chain-terminators during DNA or RNA synthesis, by binding themselves as a substrate for the target polymerase, but preventing further chain elongation. Non-nucleoside analogues may bind to allosteric sites thus influencing the local conformation of the active site via long-range conformational changes of the polymerase's structure.

Another approach whereby many antiviral compounds have been discovered is by using cell cultures infected with the virus of interest. In such cases, addition of an antiviral compound protects the cells from infection, or inhibits virus growth. For this type of experiment, it is useful to identify a large number of antiviral compounds in an efficient manner. As such, another evolving mechanism to identify new antiviral agents through the high-throughput screening ("HTS") of a large number of synthetic or natural compounds. This requires the development of an in vitro assay, which in turn requires large amounts of soluble and active protein.

When a high number of potentially antiviral compounds are tested by HTS, it is possible to identify antiviral compounds in an efficient manner. This approach has been used successfully for HIV and other viruses. However, in some cases, this approach is difficult due to the absence of a suitable system allowing infection of a cell in vitro.

In other cases, even if a suitable cell-based assay is available, this procedure may be too cumbersome or expensive. This is the case for certain dangerous viruses—such as those that require BSL-3 and/or BSL-4 facilities. Establishing a screening process for over a large amount of compounds in a BSL-3 or BSL-4 containment facility has not been achieved yet because of this heavy expense and burden. For example, flaviviruses belong to this class of viruses. These viruses require from BSL-2 to BSL-4 facilities (e.g., Dengue, WNV and/or Kyasanur Forest viruses). Thus, in such cases, it is preferable to screen potentially antiviral compounds directly on viral target proteins.

For efficiency, especially considering the difficulty with certain, more dangerous viruses, the characterization in molecular terms of the target, the viral polymerase, is of prime importance in the screening and selection of antiviral compounds. In the case of the *flavivirus* RNA polymerase ("NS5" or sometimes referred to herein as "NS5Pol"), this task has proven to be difficult for several reasons. First, polymerase genes have been notoriously difficult to clone in their entirety. When available, recombinant NS5 has been reported to be unstable in bacterial hosts. In addition, the notoriously low yield of soluble purified NS5 is a limiting factor to set up polymerase-activity assays. Another possible reason for the described difficulties is the fact that NS5 does not carry a single enzymatic activity.

Very recently, we described an N-terminal domain of NS5 (sometimes referred to herein as "NS5 methyltransferase domain") which acts as an S-adenosyl-L-methionine (AdoMet)-utilizing RNA-cap 2'Omethyltransferase, thus participating in mRNA capping, which is generally understood as the process of adding a guanosine nucleotide to the 5' end of mRNA (the methelyated end of guanosine) (Egloff & Benarroch, 2002). Additionally, we showed that the NS5 methyltransferase domain binds GTP analogues.

Due to the nature and proximity of the NS5 methyltransferase domain to the polymerase domain of the *flavivirus*, the description and characterization of the NS5 methyltransferase domain clearly shows that some nucleoside analogues and inhibitors of *flavivirus* replication could potentially be, in fact, mRNA-capping inhibitors without any effect on the polymerase activity. Likewise, it is very possible to mistakenly identify a compound as binding to NS5 and characterizing the binding data as potentially interesting for inhibition of the polymerase, but, in reality, only the RNA-capping has been affected. Therefore, it would be useful to identify and define the "junction" or sequence between the NS5 methyltransferase domain and the polymerase domain.

SUMMARY OF THE INVENTION

This invention relates to the isolation and purification of a polypeptide from a *flavivirus*.

In another aspect of the invention, the polypeptide can be separated into two domains, the N-terminal domain and the C-terminal domain, both of which are separately active.

In another aspect of the invention, the junction between the N-terminal and C-terminal domains has been identified.

In yet another aspect of the invention, the results indicated that independent expression of each of the separated domains provided greater expression than the full, unseparated polypeptide.

In still another aspect of the invention, the C-terminal of the domains in particular is purified and acts as active RNA polymerase.

In yet another aspect of the invention, the C-terminal domain demonstrates substantial homology with other RNA polymerases of clinical interest.

In still another aspect of this invention, the polymerase provides a surrogate model and system to screen synthetic and natural compounds against the polymerases of related viruses.

BRIEF DESCRIPTION OF THE FIGURES

FIG. 1 shows the sequence alignment of NS5 of *flaviviruses*: Dengue2 (SEQ ID NO. 1); Dengue3 (SEQ ID NO. 2); Dengue1 (SEQ ID NO. 3); Dengue4 (SEQ ID NO. 4); West-Nile (SEQ ID NO. 5); Kunjin (SEQ ID NO. 6); Japanese Encephalitis (SEQ ID NO. 7); Yellow Fever (SEQ ID NO. 8); Banzi (SEQ ID NO. 9); Langat (SEQ ID NO. 10); Powassan (SEQ ID NO. 11); Tick-borne Encephalitis (SEQ ID NO. 12); Louping Ill (SEQ ID NO. 13); Modoc (SEQ ID NO. 14); RioBravo (SEQ ID NO. 15).

DETAILED DESCRIPTION

Definitions

Figure 2A:
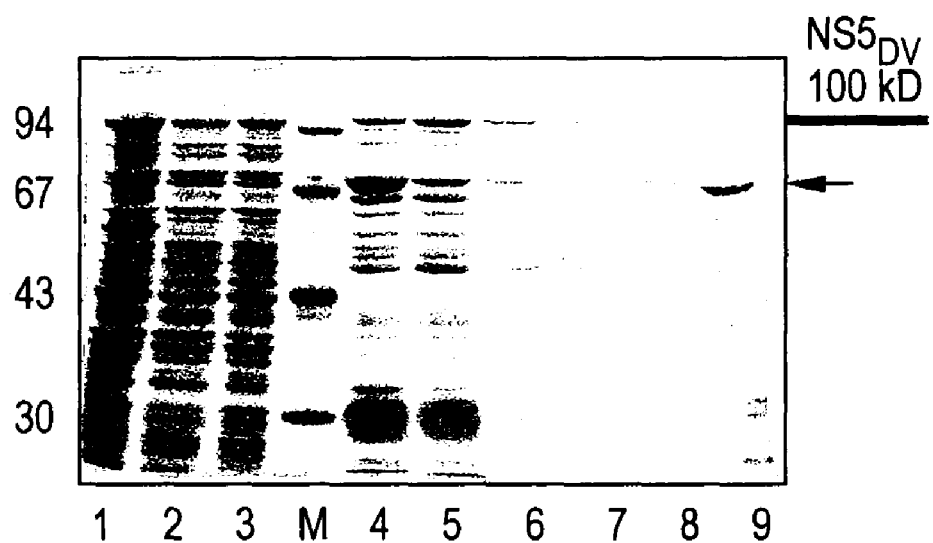
FIG. 2 shows two Western blots illustrating the expression and purification of $NS5_{DV}$ and $NS5POl_{DV}$.

"Structural equivalents" should be understood to mean a protein maintaining its conformational structure as if the protein were the native protein expressed in its natural cell.

"Substantial homology" or "substantially homologous" means a degree of homology between the isolated and described NS5Pol (as defined herein) and the RNA polymerases of other positive-single-stranded RNA viruses of clinical interest when there is homology at least about 65%, preferably at least about 70%, most preferably in excess of 80%, and even more preferably in excess of 90%, 95% or 99%.

Results and Findings

In one aspect of this invention, we discovered a way to circumvent the above-described problems associated with viral polymerase. We performed a structural analysis of *flaviviruses* NS5 genes using biocomputing methods, and isolated and defined two unique domains of NS5. As described in the literature, two distinct domains are generally defined for the large family of *flavivirus* NS5 genes, and related structural equivalents.

Specifically, as shown in the experiments, NS5 was separated into the two domains using genetic engineering techniques. We have established the independent folding of these two putative domains using various methods. Moreover, demonstrated in our experiments as set forth below, each domain is separately active, and an appropriate ligand may be mapped to either the N-terminal (capping) domain or the C-terminal (polymerase) domain of NS5. These genetic constructs allow the production of higher quantities of either domain compared to the full-length protein. Thus, simply put, the C-terminal polymerase domain of NS5 (NS5Pol) of DV (subtype 2, Strain New Guinea C), WNV (strain New York 99) and the Kunjin variant of WVN (KV) are easy to purify in large quantities, they are active as a polymerase, and constitute one aspect of our invention.

As noted, the availability of large quantities of NS5Pol allows its use as a target in HTS. One of the advantages of the isolation of the polymerase domain is that the antiviral compound, which demonstrates the modulating activity of the polymerase domain, is specific to the polymerase activity of the viral protein, without any interference of the other parts of the protein. Indeed, it is possible to detect RNA polymerase activity in a single tube using standard radioactive or nonradioactive methods.

As described herein, modulation of the polymerase activity of the protein is important in creating antiviral agents for the treatment of the enumerated viral diseases. Since DV, WNV and KV NS5Pol domains are significantly homologous to and demonstrate substantial homology with NS5Pol domains of other flaviviruses, and since DV, WNV and KV NS5Pol are functionally homologous to the RNA polymerases of other positive-single-stranded RNA viruses of clinical interest (such as the related NS5B polymerase of HCV), NS5Pol provides also a surrogate model and system to screen synthetic and natural compounds against such related viruses.

Simply put, the invention includes a method of screening antiviral compounds able to modulate the polymerase activity of significantly and functionally homologus NS5 gene encoding viruses (i.e. *flaviviruses*).
Expression and Purification Based on preceding structural and functional studies on a N-terminal methyltransferase or capping domain of protein NS5 of *flavivirus* (Egloff and Benarroch, 2002) we predicted the limit of a functional and soluble C-terminal polymerase domain of NS5. In particular, FIG. 1 identifies the sequence alignment of various *flaviviruses* as follows: Dengue 2 (P14340) (SEQ ID NO. 1), Dengue 3 (Q99D35) (SEQ ID NO. 2), Dengue 1 (Q8VBS3) (SEQ ID NO. 3), Dengue 4 (AAA42964) (SEQ ID NO. 4), West Nile virus (AAL87234) (SEQ ID NO. 5), Japanese encephalitis virus (Q82872) (SEQ ID NO. 7), Yellow fever virus (Q89277) (SEQ ID NO. 8), Banzi virus (Q67483) (SEQ ID NO. 9), Langat virus (Q9IG40) (SEQ ID NO.10), Tick-borne encephalitis virus (Q8VBS4) (SEQ ID NO. 12), Louping ill virus (O10383) (SEQ ID NO. 13), Modoc virus (CAC82912) (SEQ ID NO. 14) and Rio Bravo virus (Q9JAD5) (SEQ ID NO. 15) were aligned by ClustalW. The secondary-structure elements of the NS5MTaseDV structure as determined by X-ray crystallography and of NS5Po1DV as predicted by PredictProtein are displayed in black and red, respectively, above the sequence of NS5 Dengue. NS5Pol starts after the vertical bar just before a predicted alpha-helix. The remaining ca. 550 residues of NS5 are not shown.

As set forth above, FIG. 1 shows the sequence alignment of the N-terminal part of NS5 of several *flaviviruses* with the secondary structure elements of the capping domain of Dengue NS5 given above. Essentially, as discussed, the junction between the methyltransferase and polymerase portion of the *flaviviruses* was isolated, which allows the precise and efficient separation of the domains. The junction (or where the Pol domain starts) is located at amino acid 272.

Proteins NS5 and their corresponding Pol domains of DV, KV and WNV were expressed as recombinant proteins bearing a His-tag which facilitates subsequent purification. Accordingly, they were purified with immobilized metal-affinity chromatography (IMAC) in a first purification step. As noted above, FIG. 2 illustrates the superiority of NS5PolDV over NS5DV in terms of purification yield after IMAC following the same protocol. The results shown in FIG. 2, the expression and purification of NS5DV and NS5PolDV, were obtained as follows: NS5DV and NS5PolDV were cloned in expression plasmid pQE30, expressed in BL21[pDNAy] overnight at 17° C. after induction with 50 mM IPTG, addition of 2% EtOH and a cold shock (30 min at 4° C.). Sonication was done in 50 mM sodium phosphate lysis buffer, pH 7.5, 300 mM NaCl, 10% glycerol (10 ml of this lysis buffer for 3.6 g cell pellet) in the presence of DNAse, PMSF, protease inhibitors and lysozyme. Recombinant proteins were bound to metal-affinity-chromatography resin talon (Clontech) and eluted with 500 mM imidazole. SDS-PAGE of protein samples from expression and purification: upper panel: NS5DV, lower panel: NS5PolDV, lane 1: total fraction after lysis, lane 2: soluble fraction after lysis and centrifugation, lane 3: flowthrough of metal-affinity column, lane M: molecular mass markers, lanes 4 to 8: eluted fractions from metal-affinity column, F1 to F5, lane 9: metalaffinity resin. The corresponding molecular masses in kD of the markers are given on the left. NS5DV results in low purification yields due to instability resulting in the presence of a protein band the size of which corresponds to the polymerase domain (see arrow in the upper panel).

Figure 2B:
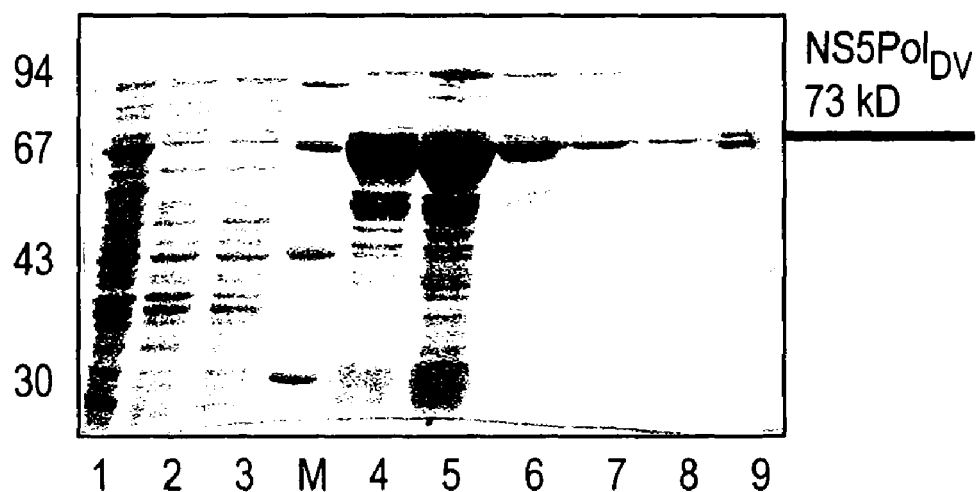

The low yield of NS5 is attributed to lower solubility of the recombinant protein and an elevated sensitivity to proteolytic cleavage during purification. This is illustrated in FIG. 2 by the presence of a cleavage product of around 73 kD which could represent the Pol domain. Yields for both proteins are compared in Table 1.

TABLE 1

Yield after expression and purification

| protein | Yield (mg per liter expression culture) | |
|---|---|---|
| | after IMAC | after heparin |
| NS5Pol$_{DV}$ | 2 | 1.2 |
| NS5$_{DV}$ | 0.2 | n.d. |
| NS5Pol$_{KV}$ | 10 | 7 |
| NS5$_{KV}$ | 7 | 0.6 |
| NS5Pol$_{WNV}$ | 12 | 8 |
| NS5$_{WNV}$ | n.d. | n.d. |

A second purification step consists of heparin affinity chromatography. The results of this purification were illustrated in FIG. 3 and obtained pursuant to the following procedure: NS5PolDV eluates from metal-affinity chromatography were dialyzed against 50 mM sodium phosphate buffer, pH 7.5, 150 mM NaCl, 10% glycerol and submitted to heparin-affinity chromatography applying a salt gradient of 150 mM to 1M NaCl. Pure protein was eluted in two peaks, at 390 mM and 460 mM NaCl.

A: SDS-PAGE of protein samples from purification steps, lane 1: pooled protein fractions from metal-affinity chromatography after dialysis, lane M: molecular mass markers, lane 2: peak 1 from heparin-affinity chromatography, lane 3: peak 2 from heparin-affinity chromatography, lane 4: flowthrough from heparin-column. The corresponding molecular masses in kD of the markers are given on the left.

B: Analytical gel filtration (Superdex 200, Pharmacia) of peak 1 and 2 of NS5PolDV from heparin affinity chromatography. The elution volume of peak 1 corresponds to the monomeric form of NS5PolDV whereas peak 2 elutes earlier corresponding to oligomeric NS5PolDV (trimer or tetramer).

Figure 3A:
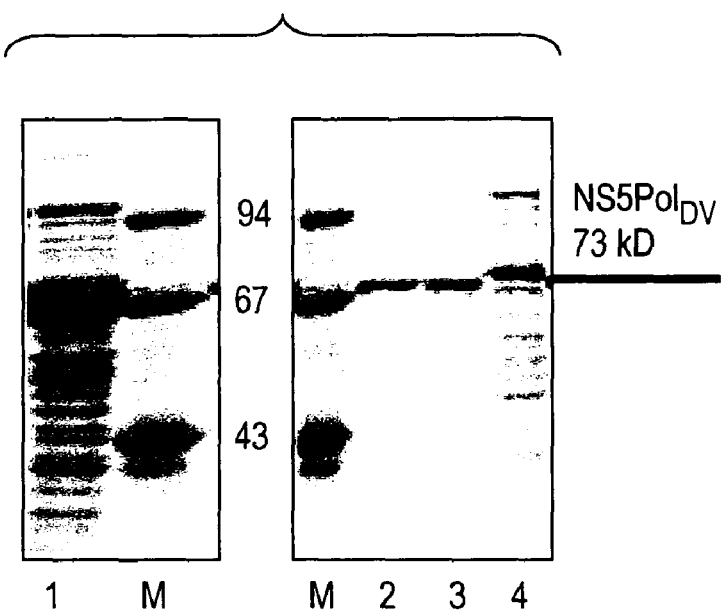
FIG. 3 shows a Western blot (FIG. 3A) and a graph (FIG. 3B) of the purified $NS5POl_{DV}$.
Figure 3B:
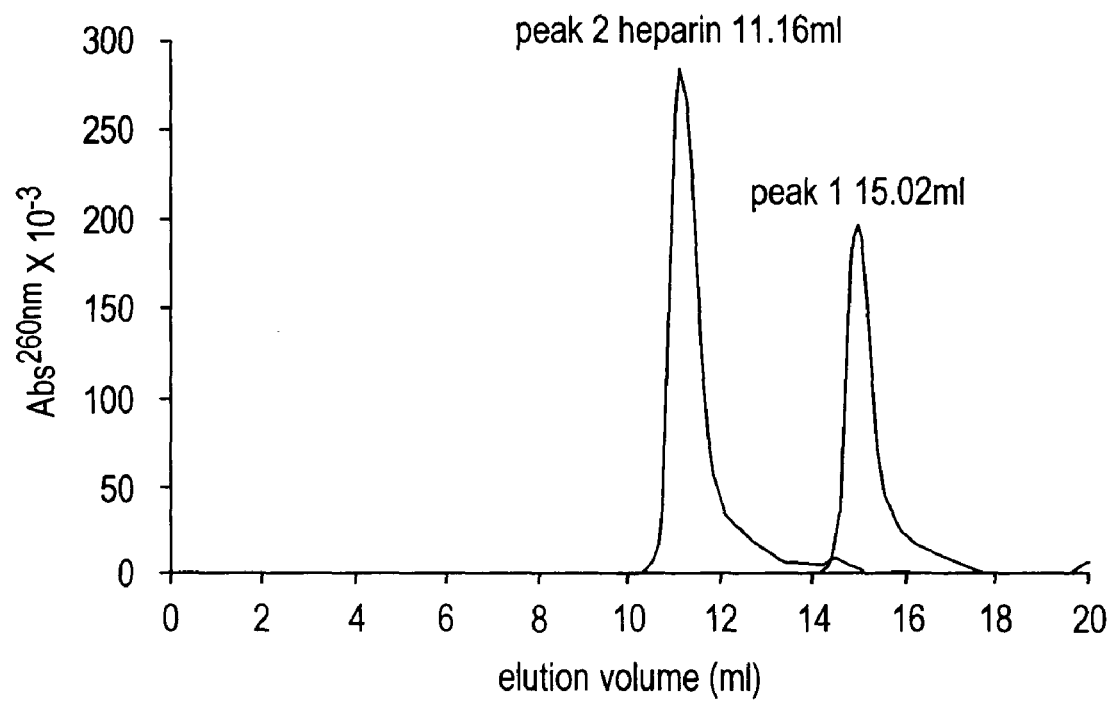

For NS5PolDV it results in two fractions eluting at different salt concentrations both representing NS5PolDV, as shown in FIG. 3A. Analytical gel filtration showed that peak 1 from heparin affinity chromatography represents the monomeric form of NS5PolDV whereas peak 2 represents an oligomeric form as shown in FIG. 3B. Both forms are purified to 98% after heparin purification step, the combined yield of NS5PolDV is 1.2 mg starting from one liter expression culture (Table 1).

Expression and purification of NS5 KV and NS5PolKV follow a similar tendency compared to Dengue NS5 (sequence identity of NS5 66.4%). Although full-length NS5 KV and NS5PolKV render considerably higher yields compared to the corresponding Dengue proteins, still, full-length NS5 KV shows lower yields after one purification step (Table 1) and, due its instability, dramatically lower yields after a second purification step. In difference to NS5PolDV, NS5PolKV elutes as a single peak after heparin affinity chromatography (data not shown). The same applies to NS5PolWNV (sequence identity to NS5PolKV 94.6%).

In all cases, the final purification product, for which the purity is adequate for HTS assays, is purified with a >10-fold increase in yield compared to the unengineered polymerase.
Activity Data Polymerase activity on NS5Pol was measured on homo- and heteropolymeric templates.

Homopolymeric Template

Activity was tested on three homopolymeric templates: poly(rC), poly(rU) and poly(rA). Only poly(rC) resulted to be a productive template for NS5PolDV. This was illustrated in FIG. 4 based on the following protocol: RNA polymerase activity was tested on a homopolymeric RNA template (polycytidylic acid, Amersham Biosciences) of an average length of 360 nt. A standard assay was carried out in 50 mM HEPES buffer, pH 8.0, 10 mM KCl, 5 mM MgCl2, 5 mM MnCl2, 10 mM DTT containing 1 µM template, 4 mM primer GG, 10 µM GTP, 0.01 mCi [3H]-GTP per µl reaction mixture and the concentration of enzyme given below. Reactions were carried out at 30° C. for given time periods and stopped by spotting a sample on DEAE filter discs (Whatman) presoaked with 50 mM EDTA. Filters were washed 3×10 min with 300 mM $(NH4)_2SO4$ buffer, pH 8.0 and 2×5 min with EtOH and air-dried. Liquid scintillation fluid was added and incorporation in counts per minute (cpm) determined by using a Wallac MicroBeta TriLux Liquid Scintillation Counter.

A: Influence of specific *E. coli* RNA polymerase inhibitor rifampicin on NS5PolDV and *E. coli* polymerase (control). NS5PolDV was tested using the conditions given above at 64-nM enzyme concentration. *E. coli* RNA polymerase was obtained from USBiochemicals and used in NS5PolDV standard reaction buffer at 37 nM.

B: Time course of [3H]-GTP incorporation by NS5PolDV peak 1 (monomeric preparation) and peak 2 (oligomeric preparation) from heparin 11 affinity chromatography (see FIG. 3A) tested at 80 nM enzyme concentration using poly (rC) without primer.

Figure 4A:
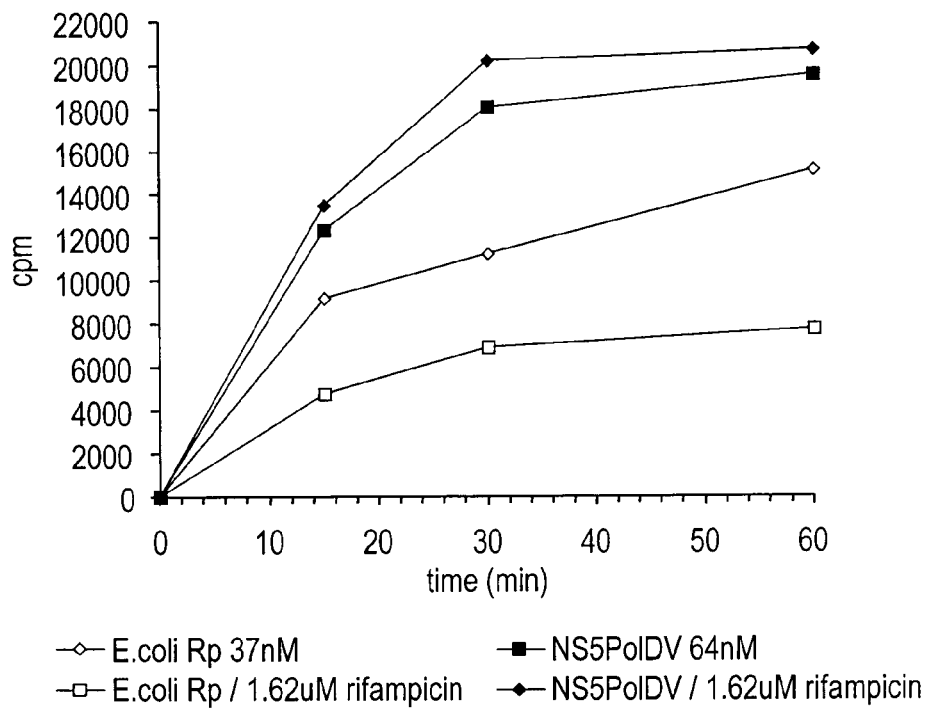
FIG. 4 shows two graphs (FIG. 4A and FIG. 4B) demonstrating the activity level of $NS5POl_{DV}$ on poly(rC).
Figure 4B:
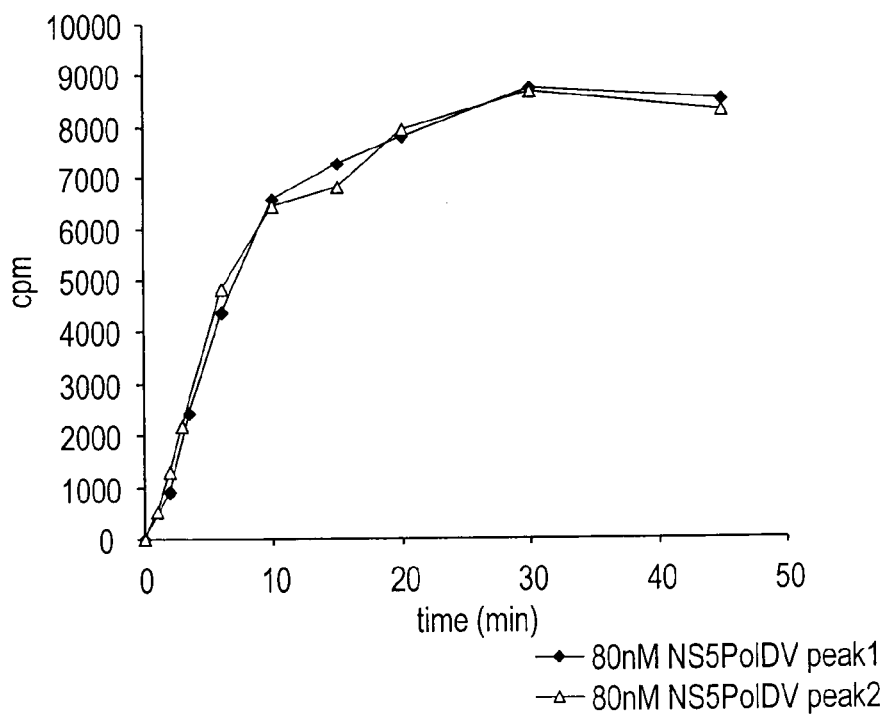

FIG. 4A shows incorporation of radioactively labeled GTP into a nascent poly(rG) polymerization product by NS5PolDV (oligomeric preparation) using primer rGG. In a control reaction *E. coli* RNA polymerase-inhibitor rifampicin was added and did not show any inhibitory effect. Thus, the observed incorporation of radioactive GTP in a polymerization product is not due to a contamination with *E. coli* RNA polymerase activity. FIG. 4B shows a parallel test of the oligomeric and monomeric preparation of NS5PolDV. In this experiment no primer was used, thus, polymerization is initiated de novo. Both preparations show identical catalytic efficiency. There are two possible explanations, either the state of oligomerization does not influence polymerase activity or under the conditions of the activity test (80 nM enzyme 6 concentration) both preparations adopt the same oligomerization state. In either way, both preparations can likewise be used for inhibitor screening studies.

In FIG. 5, the steady-state Km determination of GTP with various ligands was performed as follows: RNA polymerase activity was tested under conditions given in the description set forth above in the experiments related to FIG. 4 without the use of a primer. Initial velocities were determined over a time period of 5 min. GTP concentrations in the range of 2 to 500 µM were tested using poly(rC) at 1 µM. Template poly (rC) was tested in the range of 2 to 1000 nM with GTP fixed at 200 µM.

A: Plot of apparent intitial velocity (viapp in cpm per min) against GTP concentration. Data were fitted to a Michaelis-Menten hyperbola (viapp=Vmax[S]/(Km+[S]) using Kaleidagraph.

B: Plot of apparent initial velocity against poly(rC) concentration. Data were fitted as in A.

Figure 5A:
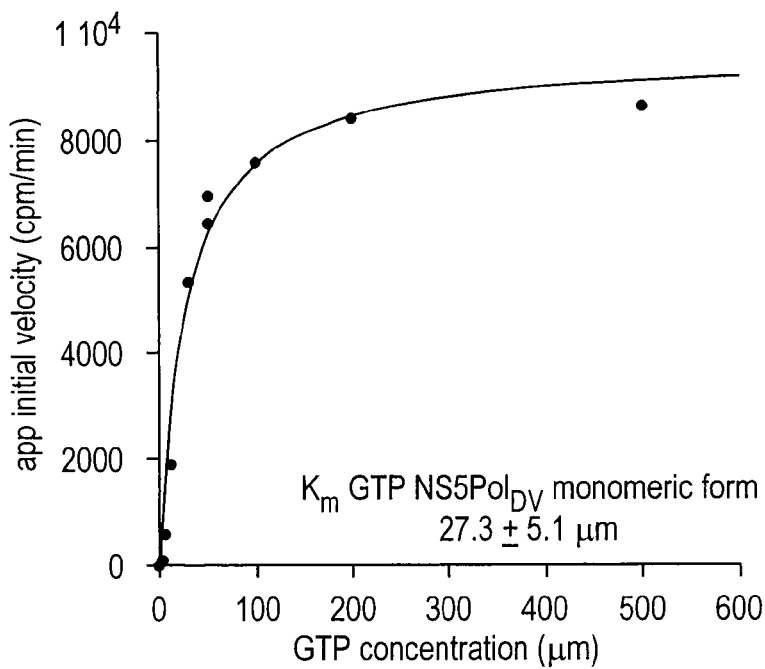
FIG. 5 shows a steady-state Km determination of GTP with and poly(rC) (in FIG. 5A) and for monomeric NS5PolDV using poly(rC) without primer (de novo initiation) (in FIG. 5B).
Figure 5B:
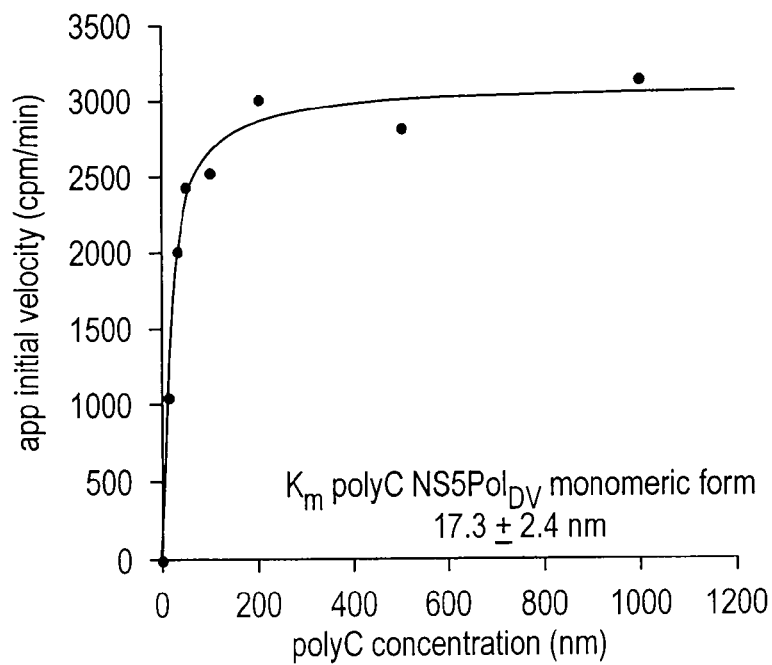

The Km of GTP was determined for NS5PolDV (monomeric preparation) as being 27.3±5.1 mM (FIG. 5A). Km values are in a similar range for the oligomeric preparation of NS5PolDV (66.2±6.6 mM) and for full-length NS5DV (13.0±2.9 mM). Thus, the affinity of NS5PolDV from both preparations versus the substrate GTP that binds to a nucleotide-binding site within the active site of the enzyme are close. This again confirms that both preparations can be used likewise. Additionally, the fact that NS5PolDV shows similar substrate affinity as NS5 indicates that the polymerase domain of *flavivirus* NS5 is a valid model system for the identification of inhibitors of the full-length protein. The Km values of polyC were determined for the monomeric preparation of NS5PolDV as 17.3±2.4 mM, the oligomeric preparation as 14.8±3.8 mM and for NS5DV as 18.0±7.3 mM. As seen above, the corresponding plot for the monomeric preparation of NS5PolDV is shown in FIG. 5B. First, this allows the conclusion that a putatively different oligomerization status of NS5PolDV does not seem to influence the affinity to a long template which could be expected to maintain cooperative interactions with two enzyme molecules at the same time. Secondly, template poly(rC) (around 360 nt long) shows identical affinity to NS5DV and NS5PolDV within the context of its use as a polymerization template. Thus, the capping domain does not seem to be involved in template binding indicating again that the isolated polymerase domain can be used for inhibitor screening experiments of the polymerase activity of full-length NS5.

Figure 6A:
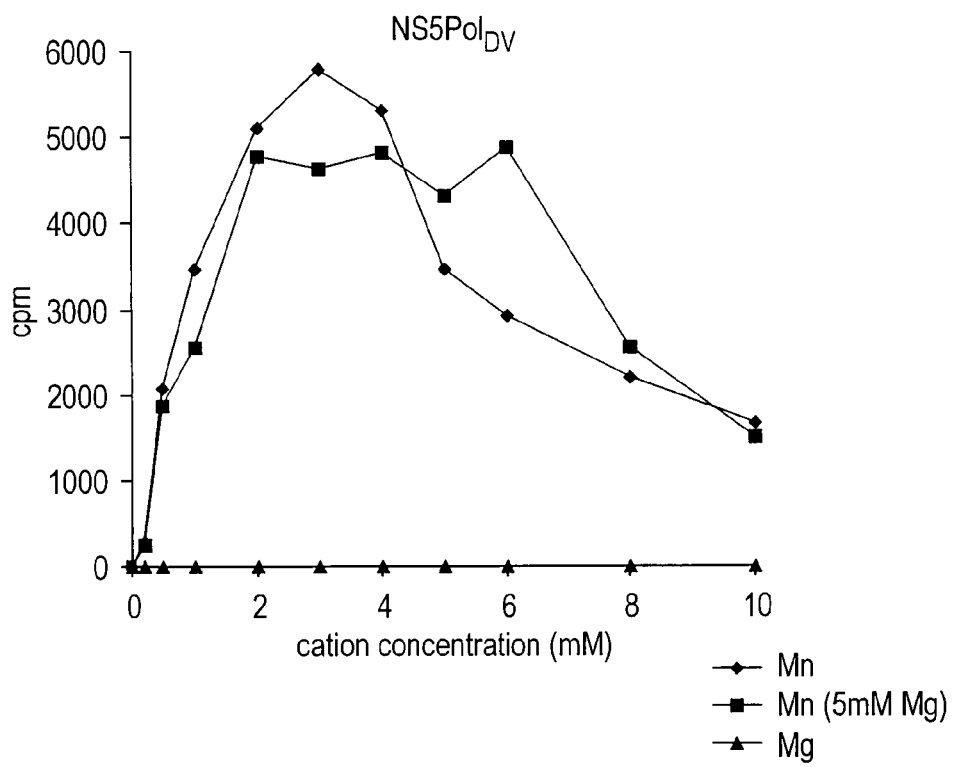
FIG. 6 shows divalent cation optimum curves for NS5PolDV and NS5PolWNV (in FIG. 6A) on poly(rC) without primer (de novo initiation) (in FIG. 6B).
Figure 6B:
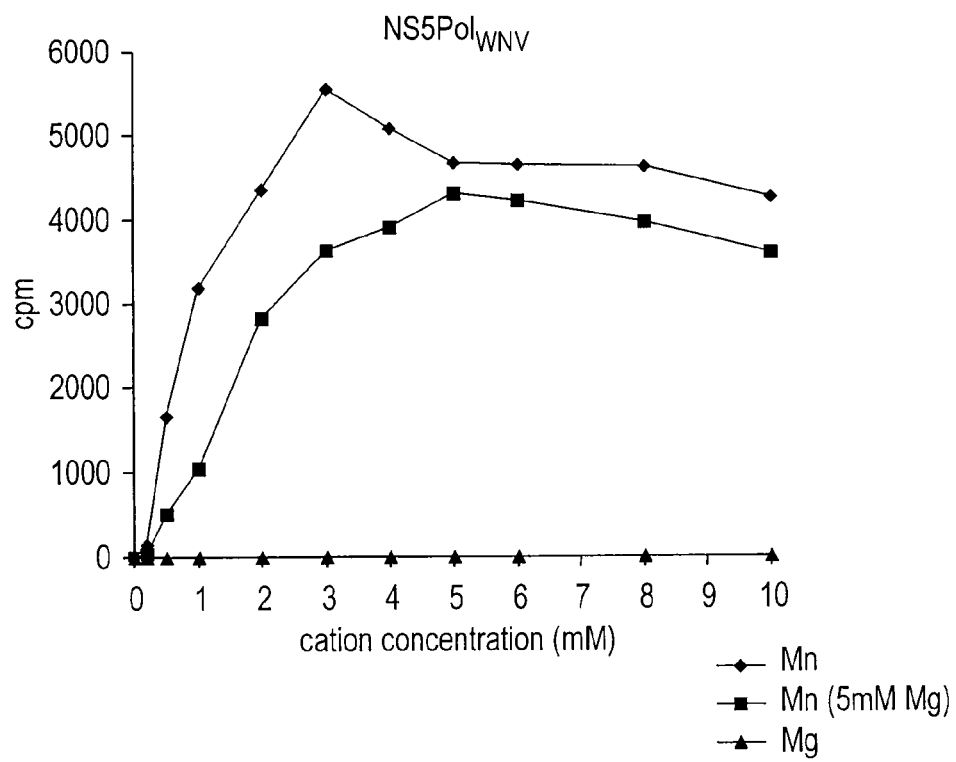

FIG. 6A shows the optimum curve for divalent manganese (Mn) and magnesium (Mg) ions of NS5PolDV on poly(rC). Polymerization on poly(rC) works exclusively in the presence of Mn ions. This is also the case for NS5PolWNV as shown in FIG. 6B. The results set forth in FIG. 6 were obtained pursuant to the following protocol:

A: Tests of NS5PolDV were carried out under standard conditions given in the description set forth above in the experiments related to FIG. 4 at 60 nM enzyme concentration. Influence of Mn2+ was tested either in absence of Mg2+ (Mn) or in presence of 5 mM Mg2+ (Mn (5 mM Mg)). Mg2+ was tested in the absence of Mn2+ (Mg).

B: Test of NS5PolWNV were carried out under the same reaction conditions as for NS5PolDV with the exception of GTP which was used at 100 µM. NS5PolWNV concentration was 400 nM.

Clearly, as seen from FIGS. 6A and 6B, the optimum curves for Mn2+ show that NS5PolWNV tolerates higher Mn2+ concentrations for the polymerization on polyC than NS5PolDV. The apparent Km value for substrate GTP is around 2 to 4-fold higher (130 mM) for NS5PolWNV and NS5PolKV in comparison to NS5PolDV (data not shown). These mechanistic differences between *flavivirus* polymerases can be studied in detail using well expressed and stable independent NS5Pol domains.

Heteropolymeric Template

NS5PolDV activity was tested on heteropolymeric specific templates comprising 717 nucleotides (225 nt of the 5' and 492 nt of the 3' of the Dengue genome). Specifically, the results are demonstrated in FIG. 7 and were obtained pursuant to the following protocol: Heteropolymeric RNA templates of 717 nt were generated by in vitro transcription using T7 RNA polymerase. The DNA template containing 225 nt of the 5' and 492 nt of the 3' of Dengue genomic RNA was constructed into plasmid pUC18. PCR products with the T7 promoter on the 5' of the positive-sense strand or the 5' of negative-sense strand were generated and used as substrates for in vitro transcription. RNA templates were replicated by NS5PolDV in 50 mM HEPES buffer, pH 8.0 containing 10 mM KCl, 10 mM DTT, 100 nM RNA template, 200 nM NS5PolDV, 500 mM ATP, UTP, GTP, 10 mM CTP and [a-$^{32}$P]-CTP at 0.1 mCi/ml. Reactions were carried out at 30° C. and stopped by spotting a sample on DEAE 12 filter discs (Whatman) pre-soaked with 50 mM EDTA. Filters were treated as explained above in the experiments related to FIG. 4.

A: Comparison of incorporation on positive-sense and complementary negative-sense minigenome RNA templates. Reactions were carried out as given above except for the use of 500 mM CTP, 50 mM GTP, 0.1 mCi/ml [a-32P]-GTP and 5 mM Mn2+.

B: Divalent-cation optimum curves on positive-sense specific RNA template. Mn2+ was used in the absence of Mg2+ and, likewise, Mg2+ in the absence of Mn2+. Reaction were stopped after 60 min. Incorporation of CMP is given in cpm. The axis on the left corresponds to values obtained in presence of Mn2+ and the axis on the right to values obtained in presence of Mg2+.

Figure 7A:
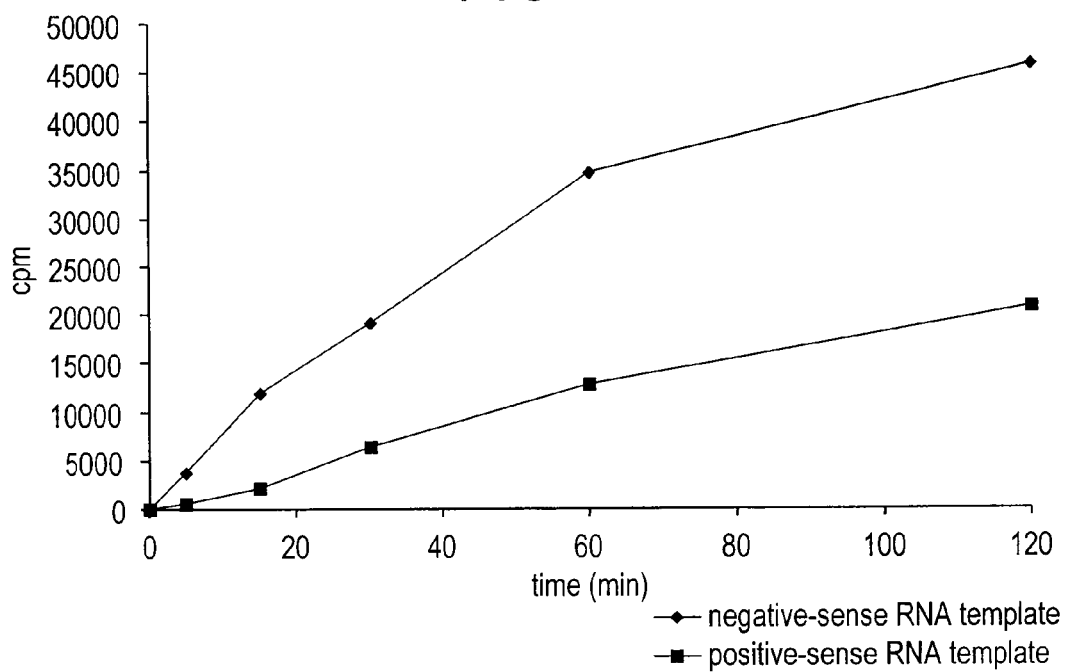
FIG. 7 shows two graphs demonstrating the activity level of NS5PolDV on specific heteropolymeric RNA templates.
Figure 7B:
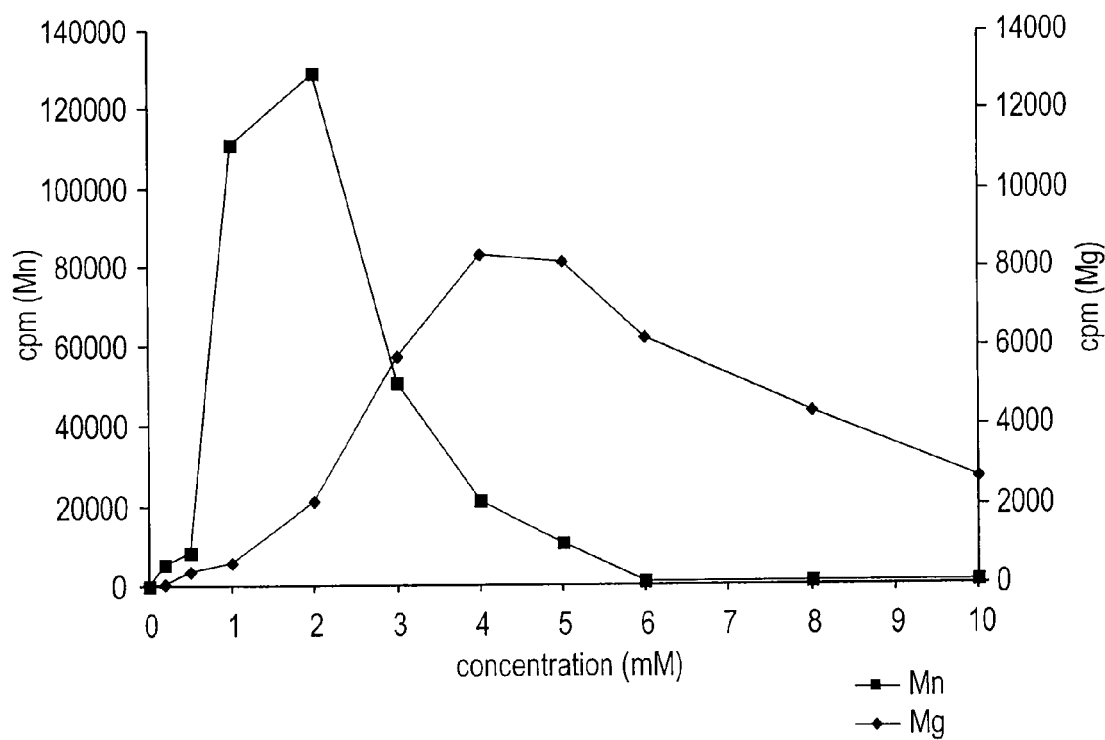

This "minigenome" template illustrated in FIG. 7 contains secondary-structure and sequence elements necessary for efficient 7 de novo initiation and replication. Positive-sense and negative-sense RNA was generated by in vitro transcription from PCR products containing the promoter for T7 RNA polymerase in either sense. Specifically, FIG. 7A illustrates that NS5PolDV replicates negative-sense mini-genome RNA with higher efficiency compared to positive-sense RNA. This observation is in accordance with the observation that 10-times more positive-sense genomic RNA is produced in Dengueinfected cells in comparison to negative-sense RNA. Optimum divalent cation concentration (Mn2+ and Mg2+) was determined for replication of the positive-sense template (FIG. 7A). NS5PolDV replicates the template with 20-fold higher efficiency at optimal Mn2+ concentration compared to optimal concentration of Mg2+. The affinity of Mn2+ to active site residues seems to be higher compared to Mg2+ as the optimum concentration is lower.

Selective Inhibition of Dengue Virus Polymerase Activity Using Nucleotide Inhibitors GTP analogs were used on NS5PolDV and NS5PolWNV to demonstrate their capacity to inhibit the NS5 polymerase domain using the homopolymeric template poly(rC). IC50 values were determined using GTP concentrations close to the determinded Km values (10 mM for NS5PolDV and 100 mM for NS5PolWNV). Table 2 shows the determined values of three putative chain terminators (3'-deoxy GTP, 3'-dioxolane 3'-deoxy GTP and 2',3'-dideoxy GTP) and 2'-O-methyl-GTP which is expected to be incorporated into the growing RNA chain, thus acting as a competitive inhibitor.

TABLE 2

IC50 values for selected GTP analogs

| inhibitor | IC50 (μM) NS5Pol$_{DV}$ | IC50 (μM) NS5Pol$_{WNV}$ |
|---|---|---|
| 3'-deoxy GTP | 0.02 | 0.18 |
| 3'-dioxolane 3'-deoxy GTP | 1.2 | 58 |
| 2',3'-dideoxy GTP | 0.8 | 30 |
| 2'-O-methyl-GTP | 5.6 | 105 |

Reactions on poly(rC) were done under conditions given in FIG. 4 without a primer. NSSPolDV was used at 60 nM. Incorporation of [3H]-GTP was measured after 15 min. Inhibitors (TriLink Corp.) were tested in the concentration range of 1 nM to 100 mM.

The capacity of 2'-O-methyl-GTP (10 mM) was compared to inhibit NS5PolDV (dimeric preparation) and full-length NS5DV. Initial velocities were determined on poly(rC) at 10 mM GTP and compared to corresponding values without inhibitor. Initial velocities were determined to be 29.3% for NS5PolDV (dimeric preparation) and 19.3% for NS5DV compared to the proteins without inhibitor. This indicates that the NS5PolDV preparation is less inhibited than the full-length polymerase. Since these inhibition results are not identical, questions related to the putative interference of the capping domain remain when using the full-length polymerase.

It is clear that the removal of the capping domain (methyltransferase domain) which is able to bind GTP and GTP analogs, at the N-terminus of NS5 provides the opportunity to obtain unambiguous data which will show that the present truncated polymerase is the target of these inhibitors. The same applies to non-nucleoside inhibitors.

CONCLUSION

To summarize our results: the polymerase domain of *flavivirus* NS5

1. is purified with higher yields than full-length NS5. The overall increase in yield of the purified product suitable for HTS assays is >10-fold, facilitating mass production for HTS assays.

2. is much more stable than full-length NS5, as less protein is lost or degraded during the course of purification, giving a cleaner and more homogeneous reagent.

3. is active on homopolymeric and heteropolymeric specific templates. Thus, the capping domain is not necessary for the polymerase activity defined as the capacity to initiate and incorporate nucleotides into RNA. The polymerase domain defined here is a bonafide polymerase useful to conduct drug-screening assays.

4. shows similar affinities for template and substrates as the full-length NS5, and is identical in all points tested in terms of polymerase activity.

5. is unambiguous about being the target of a potential inhibitor. As the capping domain is not present, inhibition of NS5 function by GTP analogues and other molecules cannot be accounted for by inhibition of the capping domain or indirect inhibition of the NS5 polymerase activity by interference of the inhibitor with the capping domain.

6. is a valid polymerase model to conduct inhibitor screening studies with the aim to identify putative inhibitors of *flavivirus* RNA polymerases.

Baginski S G, Pevear D C, Seipel M, Sun S C, Benetatos C A, Chunduru S K, Rice C M, Collett M S. "Mechanism of action of a pestivirus antiviral compound." Proc Natl Acad Sci USA 2000, 97:7981-6.

Campiani G, Fabbrini M, Morelli E, Nacci V, Greco G, Novellino E, Maga G, Spadari S, Bergamini A, Faggioli E, Uccella I, Bolacchi F, Marini S, Coletta M, Fracasso C, Caccia S. "Non-nucleoside HIV-1 reverse transcriptase inhibitors: synthesis and biological evaluation of novel quinoxalinylethylpyridylthioureas as potent antiviral agents." Antivir Chem Chemother 2000,11:141-55.

Carroll S S, Tomassini J E, Bosserman M, Getty K, Stahlhut M W, Eldrup A B, Bhat B, Hall D, Simcoe A L, LaFemina R, Rutkowski C A, Wolanski B, Yang Z, Migliaccio G, De Francesco R, Kuo L C, MacCoss M, Olsen D B. "Inhibition of hepatitis C virus RNA replication by 2'-modified nucleoside analogs." J Biol Chem 2003 278:11979-84.

De Clercq E. "Antiviral drugs: current state of the art." J. Clin. Virol. 2001:73-89.

Egloff M P, Benarroch D, Selisko B, Romette J L, Canard B. "An RNA cap (nucleoside-2'-O—)-methyltransferase in the *flavivirus* RNA polymerase NS5: crystal structure and functional characterization." EMBO J. 2002 21:2757-68.

Khandazhinskaya A L, Shirokova E A, Skoblov Y S, Victorova L S, Goryunova L Y, Beabealashvilli R S, Pronyaeva T R, Fedyuk N V, Zolin U V, Pokrovsky A G, Kukhanova M K. "Carbocyclic dinucleoside polyphosphonates: interaction with HIV reverse transcriptase and antiviral activity." J Med Chem 2002, 45:1284-91.

Lai M M. "RNA polymerase as an antiviral target of hepatitis C virus." Antivir Chem Chemother 2001,12 Suppl 1:143-7.

Mentel R, Kurek S, Wegner U, Janta-Lipinski M, Gurtler L, Matthes E. "Inhibition of adenovirus DNA polymerase by modified nucleoside triphosphate analogs correlate with their antiviral effects on cellular level." Med Microbiol Immunol (Berl) 2000,189:91-5.

Mlinaric A, Kreft S, Umek A, Strukelj B. "Screening of selected plant extracts for in vitro inhibitory activity on HIV-1 reverse transcriptase (HIV-1 RT)." Pharmazie 2000, 55:75-7.

Walker M P, Hong Z. "HCV RNA-dependent RNA polymerase as a target for antiviral development." Curr. Opinion Pharmacol. 2002, 2!:1-7.

Wang M, Ng K K, Cherney M M, Chan L, Yannopoulos C G, Bedard J, Morin N, Nguyen-Ba N, Alaoui-Ismaili M H, Bethell R C, James M N. "Non-nucleoside Analogue Inhibitors Bind to an Allosteric Site on HCV NS5B Polymerase." CRYSTAL STRUCTURES AND MECHANISM OF INHIBITION. J Biol Chem 2003 278:9489-95.

Zoulim F. "Therapy of chronic hepatitis B virus infection: inhibition of the viral polymerase and other antiviral strategies." Antiviral Res 1999, 44:1-30.

SEQUENCE LISTING

```
<160> NUMBER OF SEQ ID NOS: 30

<210> SEQ ID NO 1
<211> LENGTH: 349
<212> TYPE: PRT
<213> ORGANISM: Flavivirus sp.
<220> FEATURE:
<221> NAME/KEY: MISC_FEATURE
<223> OTHER INFORMATION: Dengue2

<400> SEQUENCE: 1

Gly Thr Gly Asn Ile Gly Glu Thr Leu Gly Glu Lys Trp Lys Ser Arg
1               5                   10                  15

Leu Asn Ala Leu Gly Lys Ser Glu Phe Gln Ile Tyr Lys Lys Ser Gly
                20                  25                  30

Ile Gln Glu Val Asp Arg Thr Leu Ala Lys Glu Gly Ile Lys Arg Gly
            35                  40                  45

Glu Thr Asp His His Ala Val Ser Arg Gly Ser Ala Lys Leu Arg Trp
        50                  55                  60

Phe Val Glu Arg Asn Met Val Thr Pro Glu Gly Lys Val Val Asp Leu
65                  70                  75                  80

Gly Cys Gly Arg Gly Gly Trp Ser Tyr Tyr Cys Gly Gly Leu Lys Asn
                85                  90                  95

Val Arg Glu Val Lys Gly Leu Thr Lys Gly Gly Pro Gly His Glu Glu
                100                 105                 110

Pro Ile Pro Met Ser Thr Tyr Gly Trp Asn Leu Val Arg Leu Gln Ser
            115                 120                 125

Gly Val Asp Val Phe Phe Thr Pro Pro Glu Lys Cys Asp Thr Leu Leu
        130                 135                 140

Cys Asp Ile Gly Glu Ser Ser Pro Asn Pro Thr Val Glu Ala Gly Arg
145                 150                 155                 160

Thr Leu Arg Val Leu Asn Leu Val Glu Asn Trp Leu Asn Asn Asn Thr
                165                 170                 175

Gln Phe Cys Ile Lys Val Leu Asn Pro Tyr Met Pro Ser Val Ile Glu
            180                 185                 190

Lys Met Glu Ala Leu Gln Arg Lys Tyr Gly Gly Ala Leu Val Arg Asn
        195                 200                 205

Pro Leu Ser Arg Asn Ser Thr His Glu Met Tyr Trp Leu Ser Asn Ala
    210                 215                 220

Ser Gly Asn Ile Val Ser Ser Val Asn Met Ile Ser Arg Met Leu Ile
225                 230                 235                 240

Asn Arg Phe Thr Met Arg His Lys Lys Ala Thr Tyr Glu Pro Asp Val
                245                 250                 255
```

```
Asp Leu Gly Ser Gly Thr Arg Asn Ile Gly Ile Glu Ser Glu Ile Pro
            260                 265                 270

Asn Leu Asp Ile Ile Gly Lys Arg Ile Glu Lys Ile Lys Gln Glu His
        275                 280                 285

Glu Thr Ser Trp His Tyr Asp Gln Asp His Pro Tyr Lys Thr Trp Ala
    290                 295                 300

Tyr His Gly Ser Tyr Glu Thr Lys Gln Thr Gly Ser Ala Ser Ser Met
305                 310                 315                 320

Gly Asn Gly Val Val Arg Leu Leu Thr Lys Pro Trp Asp Val Val Pro
                325                 330                 335

Met Val Thr Gln Met Ala Met Thr Asp Thr Thr Pro Phe
            340                 345

<210> SEQ ID NO 2
<211> LENGTH: 348
<212> TYPE: PRT
<213> ORGANISM: Flavivirus sp.
<220> FEATURE:
<221> NAME/KEY: misc_feature
<223> OTHER INFORMATION: Dengue3

```
Met Asp Val Ile Gly Glu Arg Ile Lys Arg Ile Lys Glu Glu His Ser
            275                 280                 285

Ser Thr Trp His Tyr Asp Glu Asn Pro Tyr Lys Thr Trp Ala Tyr
        290                 295                 300

His Gly Ser Tyr Glu Val Lys Ala Thr Gly Ser Ala Ser Ser Met Ile
305                 310                 315                 320

Asn Gly Val Val Lys Leu Leu Thr Lys Pro Trp Asp Val Val Pro Met
                325                 330                 335

Val Thr Gln Met Ala Met Thr Asp Thr Thr Pro Phe
            340                 345
```

```
<210> SEQ ID NO 3
<211> LENGTH: 348
<212> TYPE: PRT
<213> ORGANISM: Flavivirus sp.
<220> FEATURE:
<221> NAME/KEY: misc_feature
<223> OTHER INFORMATION: Dengue1

<400> SEQUENCE: 3
```

```
Gly Thr Gly Ala Gln Gly Glu Thr Leu Gly Glu Lys Trp Lys Arg Gln
1               5                   10                  15

Leu Asn Gln Leu Ser Lys Ser Glu Phe Asn Thr Tyr Lys Arg Ser Gly
            20                  25                  30

Ile Met Glu Val Asp Arg Ser Glu Ala Lys Glu Gly Leu Lys Arg Gly
        35                  40                  45

Glu Thr Thr Lys His Ala Val Ser Arg Gly Thr Ala Lys Leu Arg Trp
    50                  55                  60

Phe Val Glu Arg Asn Leu Val Lys Pro Glu Gly Lys Val Ile Asp Leu
65                  70                  75                  80

Gly Cys Gly Arg Gly Gly Trp Ser Tyr Tyr Cys Ala Gly Leu Lys Lys
                85                  90                  95

Val Thr Glu Val Lys Gly Tyr Thr Lys Gly Gly Pro Gly His Glu Glu
            100                 105                 110

Pro Ile Pro Met Ala Thr Tyr Gly Trp Asn Leu Val Lys Leu His Ser
        115                 120                 125

Gly Lys Asp Val Phe Phe Thr Pro Pro Glu Lys Cys Asp Thr Leu Leu
    130                 135                 140

Cys Asp Ile Gly Glu Ser Ser Pro Asn Pro Thr Ile Glu Glu Gly Arg
145                 150                 155                 160

Thr Leu Arg Val Leu Lys Met Val Glu Pro Trp Leu Arg Gly Asn Gln
                165                 170                 175

Phe Cys Ile Lys Ile Leu Asn Pro Tyr Met Pro Ser Val Val Glu Thr
            180                 185                 190

Leu Glu Gln Met Gln Arg Lys His Gly Gly Met Leu Val Arg Asn Pro
        195                 200                 205

Leu Ser Arg Asn Ser Thr His Glu Met Tyr Trp Val Ser Cys Gly Thr
    210                 215                 220

Gly Asn Ile Val Ser Ala Val Asn Met Thr Ser Arg Met Leu Leu Asn
225                 230                 235                 240

Arg Phe Thr Met Ala His Arg Lys Pro Thr Tyr Glu Arg Asp Val Asp
                245                 250                 255

Leu Gly Ala Gly Thr Arg His Val Ala Val Glu Pro Glu Val Ala Asn
            260                 265                 270

Leu Asp Ile Ile Gly Gln Arg Ile Glu Asn Ile Lys His Glu His Lys
        275                 280                 285
```

```
Ser Thr Trp His Tyr Asp Glu Asp Asn Pro Tyr Lys Thr Trp Ala Tyr
    290                 295                 300

His Gly Ser Tyr Glu Val Lys Pro Ser Gly Ser Ala Ser Ser Met Val
305                 310                 315                 320

Asn Gly Val Val Arg Leu Leu Thr Lys Pro Trp Asp Val Ile Pro Met
                325                 330                 335

Val Thr Gln Ile Ala Met Thr Asp Thr Thr Pro Phe
                340                 345

<210> SEQ ID NO 4
<211> LENGTH: 349
<212> TYPE: PRT
<213> ORGANISM: Flavivirus sp
<220> FEATURE:
<221> NAME/KEY: misc_feature
<223> OTHER INFORMATION: Dengue4

<400> SEQUENCE: 4

Gly Thr Gly Thr Thr Gly Glu Thr Leu Gly Gly Lys Trp Lys Arg Gln
1               5                   10                  15

Leu Asn Ser Leu Asp Arg Lys Glu Phe Glu Gly Tyr Lys Arg Ser Gly
                20                  25                  30

Ile Leu Glu Val Asp Arg Thr Glu Ala Lys Ser Ala Leu Lys Asp Gly
            35                  40                  45

Ser Lys Ile Lys His Ala Val Ser Arg Gly Ser Ser Lys Ile Arg Trp
    50                  55                  60

Ile Val Glu Arg Gly Met Val Lys Pro Lys Gly Lys Val Val Asp Leu
65                  70                  75                  80

Gly Cys Gly Arg Gly Gly Trp Ser Tyr Tyr Met Ala Thr Leu Lys Asn
                85                  90                  95

Val Thr Glu Val Lys Gly Tyr Thr Lys Gly Gly Pro Gly His Glu Glu
                100                 105                 110

Pro Ile Pro Met Ala Thr Tyr Gly Trp Asn Leu Val Lys Leu His Ser
            115                 120                 125

Gly Val Asp Val Phe Tyr Lys Pro Thr Glu Gln Val Asp Thr Leu Leu
    130                 135                 140

Cys Asp Ile Gly Glu Ser Ser Ser Asn Pro Thr Ile Glu Glu Gly Arg
145                 150                 155                 160

Thr Leu Arg Val Leu Lys Met Val Glu Pro Trp Leu Ser Ser Lys Pro
                165                 170                 175

Glu Phe Cys Ile Lys Val Leu Asn Pro Tyr Met Pro Thr Val Ile Glu
                180                 185                 190

Glu Leu Glu Lys Leu Gln Arg Lys His Gly Gly Asn Leu Val Arg Cys
            195                 200                 205

Pro Leu Ser Arg Asn Ser Thr His Glu Met Tyr Trp Val Ser Gly Ala
    210                 215                 220

Ser Gly Asn Ile Val Ser Ser Val Asn Thr Thr Ser Lys Met Leu Leu
225                 230                 235                 240

Asn Arg Phe Thr Thr Arg His Arg Lys Pro Thr Tyr Glu Lys Asp Val
                245                 250                 255

Asp Leu Gly Ala Gly Thr Arg Ser Val Ser Thr Glu Thr Glu Lys Pro
                260                 265                 270

Asp Met Thr Ile Ile Gly Arg Arg Leu Gln Arg Leu Gln Glu Glu His
            275                 280                 285

Lys Glu Thr Trp His Tyr Asp Gln Glu Asn Pro Tyr Arg Thr Trp Ala
    290                 295                 300
```

Tyr His Gly Ser Tyr Glu Ala Pro Ser Thr Gly Ser Ala Ser Ser Met
305                 310                 315                 320

Val Asn Gly Val Val Lys Leu Leu Thr Lys Pro Trp Asp Val Ile Pro
                325                 330                 335

Met Val Thr Gln Leu Ala Met Thr Asp Thr Thr Pro Phe
                340                 345

<210> SEQ ID NO 5
<211> LENGTH: 351
<212> TYPE: PRT
<213> ORGANISM: Flavivirus sp.
<220> FEATURE:
<221> NAME/KEY: misc_feature
<223> OTHER INFORMATION: West Nile

<400> SEQUENCE: 5

Gly Gly Ala Lys Gly Arg Thr Leu Gly Glu Val Trp Lys Glu Arg Leu
1               5                   10                  15

Asn Gln Met Thr Lys Glu Glu Phe Thr Arg Tyr Arg Lys Glu Ala Ile
                20                  25                  30

Ile Glu Val Asp Arg Ser Ala Ala Lys His Ala Arg Lys Glu Gly Asn
            35                  40                  45

Val Thr Gly Gly His Ser Val Ser Arg Gly Thr Ala Lys Leu Arg Trp
50                  55                  60

Leu Val Glu Arg Arg Phe Leu Glu Pro Val Gly Lys Val Ile Asp Leu
65                  70                  75                  80

Gly Cys Gly Arg Gly Gly Trp Cys Tyr Tyr Met Ala Thr Gln Lys Arg
                85                  90                  95

Val Gln Glu Val Arg Gly Tyr Thr Lys Gly Gly Pro Gly His Glu Glu
                100                 105                 110

Pro Gln Leu Val Gln Ser Tyr Gly Trp Asn Ile Val Thr Met Lys Ser
            115                 120                 125

Gly Val Asp Val Phe Tyr Arg Pro Ser Glu Cys Cys Asp Thr Leu Leu
130                 135                 140

Cys Asp Ile Gly Glu Ser Ser Ser Ser Ala Glu Val Glu Glu His Arg
145                 150                 155                 160

Thr Ile Arg Val Leu Glu Met Val Glu Asp Trp Leu His Arg Gly Pro
                165                 170                 175

Arg Glu Phe Cys Val Lys Val Leu Cys Pro Tyr Met Pro Lys Val Ile
                180                 185                 190

Glu Lys Met Glu Leu Leu Gln Arg Arg Tyr Gly Gly Gly Leu Val Arg
            195                 200                 205

Asn Pro Leu Ser Arg Asn Ser Thr His Glu Met Tyr Trp Val Ser Arg
210                 215                 220

Ala Ser Gly Asn Val Val His Ser Val Asn Met Thr Ser Gln Val Leu
225                 230                 235                 240

Leu Gly Arg Met Glu Lys Arg Thr Trp Lys Gly Pro Gln Tyr Glu Glu
                245                 250                 255

Asp Val Asn Leu Gly Ser Gly Thr Arg Ala Val Gly Lys Pro Leu Leu
                260                 265                 270

Asn Ser Asp Thr Ser Lys Ile Asn Asn Arg Ile Glu Arg Leu Arg Arg
            275                 280                 285

Glu Tyr Ser Ser Thr Trp His His Asp Glu Asn His Pro Tyr Arg Thr
290                 295                 300

Trp Asn Tyr His Gly Ser Tyr Asp Val Lys Pro Thr Gly Ser Ala Ser
305                 310                 315                 320

Ser Leu Val Asn Gly Val Val Arg Leu Leu Ser Lys Pro Trp Asp Thr
            325                 330                 335

Ile Thr Asn Val Thr Thr Met Ala Met Thr Asp Thr Pro Phe
        340                 345                 350

<210> SEQ ID NO 6
<211> LENGTH: 351
<212> TYPE: PRT
<213> ORGANISM: Flavivirus sp.
<220> FEATURE:
<221> NAME/KEY: misc_feature
<223> OTHER INFORMATION: Kunjin

<400> SEQUENCE: 6

Gly Gly Ala Lys Gly Arg Thr Leu Gly Glu Val Trp Lys Glu Arg Leu
1               5                   10                  15

Asn Gln Met Thr Lys Glu Glu Phe Ile Arg Tyr Arg Lys Glu Ala Ile
            20                  25                  30

Thr Glu Val Asp Arg Ser Ala Ala Lys His Ala Arg Lys Glu Arg Asn
        35                  40                  45

Ile Thr Gly Gly His Pro Val Ser Arg Gly Thr Ala Lys Leu Arg Trp
    50                  55                  60

Leu Val Glu Arg Arg Phe Leu Glu Pro Val Gly Lys Val Ile Asp Leu
65                  70                  75                  80

Gly Cys Gly Arg Gly Gly Trp Cys Tyr Tyr Met Ala Thr Gln Lys Arg
                85                  90                  95

Val Gln Glu Val Arg Gly Tyr Thr Lys Gly Gly Pro Gly His Glu Glu
            100                 105                 110

Pro Gln Leu Val Gln Ser Tyr Gly Trp Asn Ile Val Thr Met Lys Ser
        115                 120                 125

Gly Val Asp Val Phe Tyr Arg Pro Ser Glu Cys Cys Asp Thr Leu Leu
    130                 135                 140

Cys Asp Ile Gly Glu Ser Ser Ser Ala Glu Val Glu Glu His Arg
145                 150                 155                 160

Thr Leu Arg Val Leu Glu Met Val Glu Asp Trp Leu His Arg Gly Pro
                165                 170                 175

Lys Glu Phe Cys Val Lys Val Leu Cys Pro Tyr Met Pro Lys Val Ile
            180                 185                 190

Glu Lys Met Glu Leu Leu Gln Arg Arg Tyr Gly Gly Leu Val Arg
        195                 200                 205

Asn Pro Leu Ser Arg Asn Ser Thr His Glu Met Tyr Trp Val Ser Arg
    210                 215                 220

Ala Ser Gly Asn Val Val His Ser Val Asn Met Thr Ser Gln Val Leu
225                 230                 235                 240

Leu Gly Arg Met Glu Lys Lys Thr Trp Lys Gly Pro Gln Tyr Glu Glu
                245                 250                 255

Asp Val Asn Leu Gly Ser Gly Thr Arg Ala Val Gly Lys Pro Leu Leu
            260                 265                 270

Asn Ser Asp Thr Ser Lys Ile Lys Asn Arg Ile Glu Arg Leu Arg Arg
        275                 280                 285

Glu Tyr Ser Ser Thr Trp His His Asp Glu Asn His Pro Tyr Arg Thr
    290                 295                 300

Trp Asn Tyr His Gly Ser Tyr Glu Val Lys Pro Thr Gly Ser Ala Ser
305                 310                 315                 320

Ser Leu Val Asn Gly Val Val Arg Leu Leu Ser Lys Pro Trp Asp Thr
                325                 330                 335

```
Ile Thr Asn Val Thr Thr Met Ala Met Thr Asp Thr Pro Phe
            340                 345                 350
```

<210> SEQ ID NO 7
<211> LENGTH: 351
<212> TYPE: PRT
<213> ORGANISM: Flavivirus sp.
<220> FEATURE:
<221> NAME/KEY: misc_feature
<223> OTHER INFORMATION: Japanese Encephalitis

<400> SEQUENCE: 7

```
Gly Arg Pro Gly Gly Arg Thr Leu Gly Glu Gln Trp Lys Glu Lys Leu
1               5                   10                  15

Asn Ala Met Ser Arg Glu Glu Phe Phe Lys Tyr Arg Arg Glu Ala Ile
            20                  25                  30

Ile Glu Val Asp Arg Thr Glu Ala Arg Arg Ala Arg Arg Glu Asn Asn
        35                  40                  45

Ile Val Gly Gly His Pro Val Ser Arg Gly Ser Ala Lys Leu Arg Trp
    50                  55                  60

Leu Val Glu Lys Gly Phe Val Ser Pro Ile Gly Lys Val Ile Asp Leu
65                  70                  75                  80

Gly Cys Gly Arg Gly Gly Trp Ser Tyr Tyr Ala Ala Thr Leu Lys Lys
                85                  90                  95

Val Gln Glu Val Arg Gly Tyr Thr Lys Gly Gly Ala Gly His Glu Glu
            100                 105                 110

Pro Met Leu Met Gln Ser Tyr Gly Trp Asn Leu Val Ser Leu Lys Ser
        115                 120                 125

Gly Val Asp Val Phe Tyr Lys Pro Ser Glu Pro Ser Asp Thr Leu Phe
    130                 135                 140

Cys Asp Ile Gly Glu Ser Ser Pro Ser Pro Glu Val Glu Glu Gln Arg
145                 150                 155                 160

Thr Leu Arg Val Leu Glu Met Thr Ser Asp Trp Leu His Arg Gly Pro
                165                 170                 175

Arg Glu Phe Cys Ile Lys Val Leu Cys Pro Tyr Met Pro Lys Val Ile
            180                 185                 190

Glu Lys Met Glu Val Leu Gln Arg Arg Phe Gly Gly Gly Leu Val Arg
        195                 200                 205

Leu Pro Leu Ser Arg Asn Ser Asn His Glu Met Tyr Trp Val Ser Gly
    210                 215                 220

Ala Ala Gly Asn Val Val His Ala Val Asn Met Thr Ser Gln Val Leu
225                 230                 235                 240

Leu Gly Arg Met Asp Arg Thr Val Trp Arg Gly Pro Lys Tyr Glu Glu
                245                 250                 255

Asp Val Asn Leu Gly Ser Gly Thr Arg Ala Val Gly Lys Gly Glu Val
            260                 265                 270

His Ser Asn Gln Glu Lys Ile Lys Lys Arg Ile Gln Lys Leu Lys Glu
        275                 280                 285

Glu Phe Ala Thr Thr Trp His Lys Asp Pro Glu His Pro Tyr Arg Thr
    290                 295                 300

Trp Thr Tyr His Gly Ser Tyr Glu Val Lys Ala Thr Gly Ser Ala Ser
305                 310                 315                 320

Ser Leu Val Asn Gly Val Val Lys Leu Met Ser Lys Pro Trp Asp Ala
                325                 330                 335

Ile Ala Asn Val Thr Thr Met Ala Met Thr Asp Thr Pro Phe
            340                 345                 350
```

```
<210> SEQ ID NO 8
<211> LENGTH: 350
<212> TYPE: PRT
<213> ORGANISM: Flavivirus sp.
<220> FEATURE:
<221> NAME/KEY: misc_feature
<223> OTHER INFORMATION: Yellow Fever

<400> SEQUENCE: 8

Gly Thr Ala Asn Gly Lys Thr Leu Gly Glu Val Trp Lys Arg Glu Leu
1               5                   10                  15

Asn Leu Leu Asp Lys Gln Gln Phe Glu Leu Tyr Lys Arg Thr Asp Ile
            20                  25                  30

Val Glu Val Asp Arg Asp Thr Ala Arg Arg His Leu Ala Glu Gly Lys
        35                  40                  45

Val Asp Thr Gly Val Ala Val Ser Arg Gly Thr Ala Lys Leu Arg Trp
    50                  55                  60

Phe His Glu Arg Gly Tyr Val Lys Leu Glu Gly Arg Val Ile Asp Leu
65                  70                  75                  80

Gly Cys Gly Arg Gly Gly Trp Cys Tyr Tyr Ala Ala Ala Gln Lys Glu
                85                  90                  95

Val Ser Gly Val Lys Gly Phe Thr Leu Gly Arg Asp Gly His Glu Lys
            100                 105                 110

Pro Met Asn Val Gln Ser Leu Gly Trp Asn Ile Ile Thr Phe Lys Asp
        115                 120                 125

Lys Thr Asp Ile His Arg Leu Glu Pro Val Lys Cys Asp Thr Leu Leu
    130                 135                 140

Cys Asp Ile Gly Glu Ser Ser Ser Ser Ser Val Thr Glu Gly Glu Arg
145                 150                 155                 160

Thr Val Arg Val Leu Asp Thr Val Glu Lys Trp Leu Ala Cys Gly Val
                165                 170                 175

Asp Asn Phe Cys Val Lys Val Leu Ala Pro Tyr Met Pro Asp Val Leu
            180                 185                 190

Glu Lys Leu Glu Leu Leu Gln Arg Arg Phe Gly Gly Thr Val Ile Arg
        195                 200                 205

Asn Pro Leu Ser Arg Asn Ser Thr His Glu Met Tyr Tyr Val Ser Gly
    210                 215                 220

Ala Arg Ser Asn Val Thr Phe Thr Val Asn Gln Thr Ser Arg Leu Leu
225                 230                 235                 240

Met Arg Arg Met Arg Arg Pro Thr Gly Lys Val Thr Leu Glu Ala Asp
                245                 250                 255

Val Thr Leu Pro Ile Gly Thr Arg Ser Val Glu Thr Asp Lys Gly Pro
            260                 265                 270

Leu Asp Lys Glu Ala Ile Glu Glu Arg Val Glu Arg Ile Lys Ser Glu
        275                 280                 285

Tyr Met Thr Ser Trp Phe Tyr Asp Asn Asp Asn Pro Tyr Arg Thr Trp
    290                 295                 300

His Tyr Cys Gly Ser Tyr Val Thr Lys Thr Ser Gly Ser Ala Ala Ser
305                 310                 315                 320

Met Val Asn Gly Val Ile Lys Ile Leu Thr Tyr Pro Trp Asp Lys Ile
                325                 330                 335

Glu Glu Val Thr Arg Met Ala Met Thr Asp Thr Thr Pro Phe
            340                 345                 350

<210> SEQ ID NO 9
<211> LENGTH: 350
```

```
<212> TYPE: PRT
<213> ORGANISM: Flavivirus sp.
<220> FEATURE:
<221> NAME/KEY: misc_feature
<223> OTHER INFORMATION: Banzi

<400> SEQUENCE: 9

Gly Gly Ser Ser Ala Leu Thr Tyr Gly Glu Val Trp Lys Arg Gln Leu
1               5                   10                  15

Asn Leu Leu Gly Lys Gln Glu Phe Met Asn Tyr Lys Val Ser Asp Ile
            20                  25                  30

Leu Glu Val Asp Arg Ser His Ala Arg Glu Val Leu Asn Ser Gly Asn
        35                  40                  45

Asp Ala Val Gly Val Ala Val Ser Arg Gly Ser Ser Lys Leu Asn Trp
50                  55                  60

Leu Ile Glu Arg Gly Tyr Leu Arg Pro Thr Gly Arg Val Val Asp Leu
65                  70                  75                  80

Gly Cys Gly Trp Gly Gly Trp Ser Tyr Thr Cys Ala Ala Glu Arg Gln
                85                  90                  95

Val Thr Ser Val Lys Ala Tyr Thr Leu Gly Lys Glu Gly His Glu Lys
            100                 105                 110

Pro Arg Leu Ile Gln Ser Leu Gly Trp Asn Ile Ile Lys Phe Lys Asp
        115                 120                 125

Lys Ser Asp Ile Thr Arg Met Thr Pro His Ala Ser Asp Thr Leu Leu
130                 135                 140

Cys Asp Ile Gly Glu Ser Ser Ser Asn Pro Glu Val Glu Lys Glu Arg
145                 150                 155                 160

Thr Leu Arg Val Ile Glu Ala Val Glu Lys Trp Met Ser Pro Thr Thr
                165                 170                 175

Val Ser Phe Cys Phe Lys Val Leu Ala Pro Tyr Lys Pro Asp Val Ile
            180                 185                 190

Glu Ala Leu Glu Arg Phe Gln Leu Lys His Gly Gly Gly Ile Ile Arg
        195                 200                 205

Asn Pro Tyr Ser Arg Asn Ser Thr His Glu Met Tyr Tyr Val Ser Gly
210                 215                 220

Val Arg Asn Asn Ile Leu His Met Val Asn Ser Thr Ser Arg Met Leu
225                 230                 235                 240

Met Arg Arg Met Ser Arg Pro Ser Gly Arg Ser Thr Val Val Pro Asp
                245                 250                 255

Leu Ile Tyr Pro Thr Gly Thr Arg Ser Val Ala Ser Glu Ala Gly Pro
            260                 265                 270

Leu Asp Leu Glu Lys Val Lys Ala Arg Ile Asn Arg Leu Lys Glu Glu
        275                 280                 285

Gln Glu Ser Thr Trp Phe Val Asp Ser Asp His Pro Tyr Arg Thr Trp
290                 295                 300

His Tyr His Gly Ser Tyr Val Ala Lys Gln Ser Gly Thr Ala Ala Ser
305                 310                 315                 320

Met Ile Asn Gly Val Val Lys Leu Leu Ser Gly Pro Trp Asp Arg Ile
                325                 330                 335

Glu Glu Val Thr Asn Met Ala Met Thr Asp Thr Thr Pro Phe
            340                 345                 350

<210> SEQ ID NO 10
<211> LENGTH: 350
<212> TYPE: PRT
<213> ORGANISM: Flavivirus sp.
<220> FEATURE:
```

<221> NAME/KEY: misc_feature
<223> OTHER INFORMATION: Langat

<400> SEQUENCE: 10

Gly Gly Ser Glu Gly Asp Thr Leu Gly Asp Met Trp Lys Ala Arg Leu
1               5                   10                  15

Asn Ser Cys Thr Lys Glu Glu Phe Phe Ala Tyr Arg Arg Ala Gly Val
            20                  25                  30

Met Glu Thr Asp Arg Glu Lys Ala Arg Glu Leu Leu Lys Arg Gly Glu
        35                  40                  45

Thr Asn Met Gly Leu Ala Val Ser Arg Gly Thr Ser Lys Leu Ala Trp
    50                  55                  60

Met Glu Glu Arg Gly Tyr Val Thr Leu Lys Gly Glu Val Val Asp Leu
65                  70                  75                  80

Gly Cys Gly Arg Gly Gly Trp Ser Tyr Tyr Ala Ala Ser Arg Pro Ala
                85                  90                  95

Val Met Ser Val Arg Ala Tyr Thr Ile Gly Gly Lys Gly His Glu Ser
            100                 105                 110

Pro Arg Met Val Thr Ser Leu Gly Trp Asn Leu Ile Lys Phe Arg Ala
        115                 120                 125

Gly Met Asp Val Phe Ser Met Glu Pro His Arg Ala Asp Ala Ile Leu
    130                 135                 140

Cys Asp Ile Gly Glu Ser Asn Pro Asp Ala Val Val Glu Gly Glu Arg
145                 150                 155                 160

Ser Arg Arg Val Ile Leu Leu Met Glu Gln Trp Lys Asn Arg Asn Pro
                165                 170                 175

Thr Ala Thr Cys Val Phe Lys Val Leu Ala Pro Tyr Arg Pro Glu Val
            180                 185                 190

Ile Glu Ala Leu His Arg Phe Gln Leu Gln Trp Gly Gly Gly Leu Val
        195                 200                 205

Arg Thr Pro Phe Ser Arg Asn Ser Thr His Glu Met Tyr Phe Ser Thr
    210                 215                 220

Ala Ile Thr Gly Asn Ile Val Asn Ser Val Asn Ile Gln Ser Arg Lys
225                 230                 235                 240

Leu Leu Ala Arg Phe Gly Asp Gln Arg Gly Pro Thr Arg Val Pro Glu
                245                 250                 255

Ile Asp Leu Gly Val Gly Thr Arg Cys Val Val Leu Ala Glu Asp Lys
            260                 265                 270

Val Lys Glu Lys Asp Val Met Glu Arg Ile Gln Ala Leu Lys Asp Gln
        275                 280                 285

Tyr Cys Asp Thr Trp His Glu Asp His Glu His Pro Tyr Arg Thr Trp
    290                 295                 300

Gln Tyr Trp Gly Ser Tyr Lys Thr Ala Ala Thr Gly Ser Ser Ala Ser
305                 310                 315                 320

Leu Leu Asn Gly Val Val Lys Leu Leu Ser Trp Pro Trp Asn Ala Arg
                325                 330                 335

Glu Asp Val Val Arg Met Ala Met Thr Asp Thr Thr Ala Phe
            340                 345                 350

<210> SEQ ID NO 11
<211> LENGTH: 350
<212> TYPE: PRT
<213> ORGANISM: Flavivirus sp.
<220> FEATURE:
<221> NAME/KEY: misc_feature
<223> OTHER INFORMATION: Powassan

<400> SEQUENCE: 11

```
Gly Gly Ala Glu Gly Ser Thr Leu Gly Asp Ile Trp Lys Gln Arg Leu
1               5                   10                  15
Asn Ser Cys Thr Lys Glu Glu Phe Phe Ala Tyr Arg Arg Thr Gly Val
            20                  25                  30
Met Glu Thr Asn Arg Asp Gln Ala Arg Glu Leu Leu Arg Arg Gly Glu
        35                  40                  45
Thr Asn Met Gly Leu Ala Val Ser Arg Gly Cys Ala Lys Leu Ala Trp
    50                  55                  60
Leu Glu Glu Arg Gly Tyr Ala Thr Leu Lys Gly Glu Val Val Asp Leu
65                  70                  75                  80
Gly Cys Gly Arg Gly Gly Trp Ser Tyr Tyr Ala Ala Ser Arg Pro Ser
                85                  90                  95
Val Met Ala Val Arg Ala Tyr Thr Ile Gly Gly Lys Gly His Glu Ala
            100                 105                 110
Pro Arg Leu Val Thr Ser Leu Gly Trp Asn Leu Ile Lys Phe Arg Ser
        115                 120                 125
Gly Met Asp Val Phe Ser Met Ala Thr Thr Arg Ala Asp Thr Ile Leu
    130                 135                 140
Cys Asp Ile Gly Glu Ser Ser Pro Asp Pro Glu Lys Glu Gly Ala Arg
145                 150                 155                 160
Ser Arg Arg Val Ile Leu Leu Met Glu Gln Trp Lys Ala Arg Asn Pro
                165                 170                 175
Asp Ala Ala Ala Val Phe Lys Val Leu Ala Pro Tyr Arg Pro Glu Val
            180                 185                 190
Leu Glu Ala Leu His Arg Phe Gln Leu Gln Trp Gly Gly Gly Leu Val
        195                 200                 205
Arg Val Pro Phe Ser Arg Asn Ser Thr His Glu Met Tyr Tyr Ser Thr
    210                 215                 220
Ala Val Thr Gly Asn Leu Val Asn Ser Val Asn Val Leu Ser Arg Lys
225                 230                 235                 240
Leu Leu Ala Arg Phe Gly Glu Thr Arg Gly Pro Ile Gln Val Pro Glu
                245                 250                 255
Ile Asp Leu Gly Thr Gly Thr Arg Cys Val Thr Leu Ala Glu Asp Lys
            260                 265                 270
Val Lys Pro Arg Asp Val Ala Glu Arg Ile Gly Ala Leu Arg Glu Gln
        275                 280                 285
Tyr Ser Glu Ser Trp His Glu Asp Lys Glu His Pro Tyr Arg Thr Trp
    290                 295                 300
Gln Tyr Trp Gly Ser Tyr Arg Thr Pro Ala Thr Gly Ser Ala Ala Ser
305                 310                 315                 320
Leu Ile Asn Gly Val Val Lys Leu Leu Ser Trp Pro Trp Asn Ala Arg
                325                 330                 335
Glu Asp Val Thr Arg Met Ala Met Thr Asp Thr Thr Ala Phe
            340                 345                 350
```

<210> SEQ ID NO 12
<211> LENGTH: 350
<212> TYPE: PRT
<213> ORGANISM: Flavivirus sp.
<220> FEATURE:
<221> NAME/KEY: misc_feature
<223> OTHER INFORMATION: Tick-borne Encephalitis

<400> SEQUENCE: 12

```
Gly Gly Ser Glu Gly Asp Thr Leu Gly Asp Leu Trp Lys Arg Arg Leu
```

```
              1               5                  10                 15
Asn Gly Cys Thr Lys Glu Glu Phe Phe Ala Tyr Arg Arg Thr Gly Ile
                 20                 25                 30

Leu Glu Thr Glu Arg Asp Lys Ala Arg Glu Leu Leu Arg Arg Gly Glu
                 35                 40                 45

Thr Asn Met Gly Leu Ala Val Ser Arg Gly Thr Ala Lys Leu Ala Trp
                 50                 55                 60

Leu Glu Glu Arg Gly Tyr Ala Thr Leu Lys Gly Glu Val Val Asp Leu
 65                 70                 75                 80

Gly Cys Gly Arg Gly Gly Trp Ser Tyr Tyr Ala Ala Ser Arg Pro Ala
                 85                 90                 95

Val Met Ser Val Lys Ala Tyr Thr Ile Gly Gly Lys Gly His Glu Thr
                100                105                110

Pro Lys Met Val Thr Ser Leu Gly Trp Asn Leu Ile Lys Phe Arg Ala
                115                120                125

Gly Val Asp Val Phe Ser Met Gln Pro His Arg Ala Asp Thr Ile Met
                130                135                140

Cys Asp Ile Gly Glu Ser Asn Pro Asp Ala Val Val Glu Gly Glu Arg
145                150                155                160

Thr Arg Lys Val Ile Leu Leu Met Glu Gln Trp Lys Asn Arg Asn Pro
                165                170                175

Thr Ala Thr Cys Val Phe Lys Val Leu Ala Pro Tyr Arg Pro Glu Val
                180                185                190

Ile Glu Ala Leu His Arg Phe Gln Leu Gln Trp Gly Gly Gly Leu Val
                195                200                205

Arg Thr Pro Phe Ser Arg Asn Ser Thr His Glu Met Tyr Tyr Ser Thr
210                215                220

Ala Val Thr Gly Asn Ile Val Asn Ser Val Asn Ile Gln Ser Arg Lys
225                230                235                240

Leu Leu Ala Arg Phe Gly Asp Gln Arg Gly Pro Thr Arg Val Pro Glu
                245                250                255

Leu Asp Leu Gly Val Gly Thr Arg Cys Val Val Leu Ala Glu Asp Lys
                260                265                270

Val Lys Glu Lys Asp Val Gln Glu Arg Ile Ser Ala Leu Arg Glu Gln
                275                280                285

Tyr Gly Glu Thr Trp His Met Asp Arg Glu His Pro Tyr Arg Thr Trp
                290                295                300

Gln Tyr Trp Gly Ser Tyr Arg Thr Ala Pro Thr Gly Ser Ala Ala Ser
305                310                315                320

Leu Ile Asn Gly Val Val Lys Leu Leu Ser Trp Pro Trp Asn Ala Arg
                325                330                335

Glu Asp Val Val Arg Met Ala Met Thr Asp Thr Thr Ala Phe
                340                345                350

<210> SEQ ID NO 13
<211> LENGTH: 350
<212> TYPE: PRT
<213> ORGANISM: Flavivirus sp.
<220> FEATURE:
<221> NAME/KEY: misc_feature
<223> OTHER INFORMATION: LoupingIll

<400> SEQUENCE: 13

Gly Gly Ser Asp Gly Asp Thr Leu Gly Asp Leu Trp Lys Arg Arg Leu
 1               5                  10                 15

Asn Asn Cys Thr Lys Glu Glu Phe Phe Val Tyr Arg Arg Thr Gly Ile
```

```
            20                  25                  30
Leu Glu Thr Glu Arg Asp Lys Ala Arg Glu Leu Leu Arg Arg Gly Glu
        35                  40                  45

Thr Asn Met Gly Leu Ala Val Ser Arg Gly Thr Ala Lys Leu Ala Trp
 50                  55                  60

Leu Glu Glu Arg Gly Tyr Arg Thr Leu Lys Gly Glu Val Val Asp Leu
65                  70                  75                  80

Gly Cys Gly Arg Gly Gly Trp Ser Tyr Tyr Ala Ala Ser Arg Pro Ala
                85                  90                  95

Val Met Ser Val Arg Ala Tyr Thr Ile Gly Gly Arg Gly His Glu Val
                100                 105                 110

Pro Lys Met Val Thr Ser Leu Gly Trp Asn Leu Ile Arg Phe Arg Ser
            115                 120                 125

Gly Met Asp Val Phe Ser Met Gln Pro His Arg Ala Asp Thr Ile Met
        130                 135                 140

Cys Asp Ile Gly Glu Ser Asn Pro Asp Ala Ala Val Glu Gly Glu Arg
145                 150                 155                 160

Thr Arg Lys Val Ile Ser Leu Met Glu Gln Trp Lys Ile Arg Asn Pro
                165                 170                 175

Ala Ala Ala Cys Val Phe Lys Val Leu Ala Pro Tyr Arg Pro Glu Val
                180                 185                 190

Ile Glu Ala Leu His Arg Phe Gln Leu Gln Trp Gly Gly Gly Leu Val
            195                 200                 205

Arg Thr Pro Phe Ser Arg Asn Ser Thr His Glu Met Tyr Tyr Ser Thr
        210                 215                 220

Ala Val Thr Gly Asn Ile Val Asn Ser Val Asn Ile Gln Ser Arg Lys
225                 230                 235                 240

Leu Leu Ala Arg Phe Gly Asp Gln Arg Gly Pro Thr Lys Val Pro Glu
                245                 250                 255

Ala Asp Leu Gly Val Gly Thr Arg Cys Val Val Leu Ala Glu Asp Lys
                260                 265                 270

Val Lys Glu Gln Asp Val Gln Glu Arg Ile Arg Ala Leu Arg Lys Gln
            275                 280                 285

Tyr Ser Glu Thr Trp His Met Asp Glu Glu His Pro Tyr Arg Thr Trp
        290                 295                 300

Gln Tyr Trp Gly Thr Ser Arg Thr Ala Pro Thr Gly Ser Ala Ala Ser
305                 310                 315                 320

Leu Ile Asn Gly Val Val Lys Leu Leu Ser Trp Pro Trp Asn Ala Arg
                325                 330                 335

Glu Asp Val Val Arg Met Ala Met Thr Asp Thr Thr Ala Phe
                340                 345                 350

<210> SEQ ID NO 14
<211> LENGTH: 352
<212> TYPE: PRT
<213> ORGANISM: Flavivirus sp.
<220> FEATURE:
<221> NAME/KEY: misc_feature
<223> OTHER INFORMATION: Modoc

<400> SEQUENCE: 14

Arg Gly Ile Cys Ser Ser Ala Pro Thr Leu Gly Glu Ile Trp Lys Arg
1               5                   10                  15

Lys Leu Asn Gln Leu Asp Ala Lys Glu Phe Met Ala Tyr Arg Arg Arg
            20                  25                  30

Phe Val Val Glu Val Asp Arg Asn Glu Ala Arg Glu Ala Leu Ala Lys
```

-continued

```
        35                  40                  45

Gly Lys Thr Asn Thr Gly His Ala Val Ser Arg Gly Thr Ala Lys Leu
    50                  55                  60

Ala Trp Ile Asp Glu Arg Gly Gly Val Glu Leu Lys Gly Ser Val Val
65                  70                  75                  80

Asp Leu Gly Cys Gly Arg Gly Gly Trp Ser Tyr Tyr Ala Ala Ser Gln
                85                  90                  95

Pro Asn Val Arg Glu Val Lys Ala Tyr Thr Leu Gly Thr Ser Gly His
            100                 105                 110

Glu Lys Pro Arg Leu Val Glu Thr Phe Gly Trp Asn Leu Ile Thr Phe
        115                 120                 125

Lys Ser Lys Val Asp Val Arg Lys Met Glu Pro Phe Gln Ala Asp Thr
    130                 135                 140

Val Leu Cys Asp Ile Gly Glu Ser Asn Pro Thr Ala Ala Val Glu Ala
145                 150                 155                 160

Ser Arg Thr Leu Thr Val Leu Asn Val Ile Ser Arg Trp Leu Glu Tyr
                165                 170                 175

Asn Gln Gly Cys Gly Phe Cys Val Lys Val Leu Asn Pro Tyr Ser Cys
            180                 185                 190

Asp Val Leu Glu Ala Leu Met Lys Met Gln Arg Arg Phe Gly Gly Gly
        195                 200                 205

Leu Ile Arg Val Pro Leu Ser Arg Asn Ser Thr His Glu Met Tyr Phe
    210                 215                 220

Val Ser Gly Ile Lys Asn Asn Ile Met Gly Asn Val Thr Ala Val Ser
225                 230                 235                 240

Arg Gln Leu Leu Lys Arg Met Glu Glu Gln Gly Gly Glu Arg Val Val
                245                 250                 255

Pro Asp Tyr Lys Phe Ser Thr Gly Thr Arg Ser Asn Leu Thr Gln Lys
            260                 265                 270

Ile Glu Val Pro Glu Glu Glu Val Gln Met Arg Val Asp Lys Ile Lys
        275                 280                 285

Ala Glu Lys Ser Gly Thr Trp Cys Phe Asp Ser Asn His Pro Tyr Arg
    290                 295                 300

Thr Trp Asn Tyr His Gly Ser Tyr Arg Val Arg Asp Val Gly Thr Arg
305                 310                 315                 320

Ala Ser Ala Val Asn His Val Val Lys Leu Leu Ser Trp Pro Trp Gly
                325                 330                 335

Lys Met Glu Lys Val Leu Ala Met Ser Met Thr Asp Thr Thr Ala Phe
            340                 345                 350

<210> SEQ ID NO 15
<211> LENGTH: 352
<212> TYPE: PRT
<213> ORGANISM: Flavivirus sp.
<220> FEATURE:
<221> NAME/KEY: misc_feature
<223> OTHER INFORMATION: RioBravo

<400> SEQUENCE: 15

Arg Gly Val Ser Ser Ser Tyr Ile Thr Tyr Gly Glu Gln Trp Lys Arg
1               5                   10                  15

Glu Leu Asn Lys Leu Asn Ala Gln Ala Phe Phe Leu Tyr Lys Ser Arg
            20                  25                  30

Leu Val His Glu Ile Asp Arg Ala Glu Ala Val Ser Asn Leu Ser Lys
        35                  40                  45

Gly Arg Thr Asn Thr Gly His Ala Val Ser Arg Gly Thr Ser Lys Leu
```

-continued

```
            50                  55                  60
Ala Trp Met His Glu Arg Gly Tyr Val Pro Leu Lys Gly Val Val
 65                  70                  75                  80

Asp Leu Gly Ser Gly Arg Gly Gly Trp Ser Tyr Tyr Ala Ala Gln
                 85                  90                  95

Glu Arg Val Arg Lys Val Asn Ala Tyr Thr Leu Ala Thr Thr Lys Gly
                    100                 105                 110

His Glu Gln Pro Arg Leu Val Gln Ser Tyr Gly Trp Asn Leu Val Thr
                    115                 120                 125

Phe Lys Lys Ala Asp Val Arg Thr Ile Glu Pro Tyr Pro Val Asp Thr
130                 135                 140

Leu Leu Cys Asp Ile Gly Glu Ser Ser Ser Ser Ser Ile Glu Ala
145                 150                 155                 160

Lys Arg Thr Leu Gln Ile Met Asp Val Val Gly Lys Trp Leu Glu Ile
                    165                 170                 175

Ser Pro Gly Ala Ser Phe Cys Ile Lys Ile Leu Cys Pro Tyr Asn Pro
                    180                 185                 190

Glu Val Ile Glu His Leu Ser Arg Trp Gln His Gln Phe Gly Gly Gly
                    195                 200                 205

Leu Val Arg Val Pro His Ser Arg Asn Ser Thr His Glu Met Tyr Phe
210                 215                 220

Val Ser Gly Gly Gly Asn Leu Met Ser Ile Thr Ala Val Thr
225                 230                 235                 240

Thr Gln Leu Met Arg Arg Phe Thr Leu Glu Ala Gly Pro Arg His Val
                    245                 250                 255

Phe Asp Ile Asn Leu Gly Val Gly Thr Arg Ser Asn Leu Met Glu Lys
                    260                 265                 270

Ser Glu Ala Asp Lys Ser Leu Ile Ala Asp Arg Ile Thr Ile Ile Gln
                    275                 280                 285

Asn Glu Asn Lys Ala Ser Trp His Gln Asp Pro Asn Gln Pro Tyr Arg
                    290                 295                 300

Thr Trp Thr Tyr His Gly Ser Tyr Ser Ile Arg Asp Val Gly Thr Ser
305                 310                 315                 320

Ala Ser Ala Pro Asn His Val Val Lys Leu Leu Ala Trp Pro Trp Leu
                    325                 330                 335

Lys Ile Glu Lys Val Val Leu Met Ala Met Thr Asp Thr Thr Ala Phe
                    340                 345                 350
```

<210> SEQ ID NO 16
<211> LENGTH: 629
<212> TYPE: PRT
<213> ORGANISM: Flavivirus sp.
<220> FEATURE:
<221> NAME/KEY: misc_feature
<223> OTHER INFORMATION: Dengue2

<400> SEQUENCE: 16

```
Pro Asn Leu Asp Ile Ile Gly Lys Arg Ile Glu Lys Ile Lys Gln Glu
 1               5                  10                  15

His Glu Thr Ser Trp His Tyr Asp Gln Asp His Pro Tyr Lys Thr Trp
                 20                  25                  30

Ala Tyr His Gly Ser Tyr Glu Thr Lys Gln Thr Gly Ser Ala Ser Ser
                 35                  40                  45

Met Gly Asn Gly Val Val Arg Leu Leu Thr Lys Pro Trp Asp Val Val
 50                  55                  60

Pro Met Val Thr Gln Met Ala Met Thr Asp Thr Thr Pro Phe Gly Gln
```

-continued

```
                65                  70                  75                  80
            Gln Arg Val Phe Lys Glu Lys Val Asp Thr Arg Thr Gln Glu Pro Lys
                                85                  90                  95

Glu Gly Thr Lys Lys Leu Met Lys Ile Thr Ala Glu Trp Leu Trp Lys
                               100                 105                 110

Glu Leu Gly Lys Lys Lys Thr Pro Arg Met Cys Thr Arg Glu Glu Phe
                               115                 120                 125

Thr Arg Lys Val Arg Ser Asn Ala Ala Leu Gly Ala Ile Phe Thr Asp
                               130                 135                 140

Glu Asn Lys Trp Lys Ser Ala Arg Glu Ala Val Glu Asp Ser Arg Phe
            145                 150                 155                 160

Trp Glu Leu Val Asp Lys Glu Arg Asn Leu His Leu Glu Gly Lys Cys
                               165                 170                 175

Glu Thr Cys Val Tyr Asn Met Met Gly Lys Arg Glu Lys Lys Leu Gly
                               180                 185                 190

Glu Phe Gly Lys Ala Lys Gly Ser Arg Ala Ile Trp Tyr Met Trp Leu
                               195                 200                 205

Gly Ala Arg Phe Leu Glu Phe Glu Ala Leu Gly Phe Leu Asn Glu Asp
                               210                 215                 220

His Trp Phe Ser Arg Glu Asn Ser Leu Ser Gly Val Glu Gly Glu Gly
            225                 230                 235                 240

Leu His Lys Leu Gly Tyr Ile Leu Arg Asp Val Ser Lys Lys Glu Gly
                               245                 250                 255

Gly Ala Met Tyr Ala Asp Asp Thr Ala Gly Trp Asp Thr Arg Ile Thr
                               260                 265                 270

Leu Glu Asp Leu Lys Asn Glu Glu Met Val Thr Asn His Met Glu Gly
                               275                 280                 285

Glu His Lys Lys Leu Ala Glu Ala Ile Phe Lys Leu Thr Tyr Gln Asn
                               290                 295                 300

Lys Val Val Arg Val Gln Arg Pro Thr Pro Arg Gly Thr Val Met Asp
            305                 310                 315                 320

Ile Ile Ser Arg Arg Asp Gln Arg Gly Ser Gly Gln Val Gly Thr Tyr
                               325                 330                 335

Gly Leu Asn Thr Phe Thr Asn Met Glu Ala Gln Leu Ile Arg Gln Met
                               340                 345                 350

Glu Gly Glu Gly Val Phe Lys Ser Ile Gln His Leu Thr Val Thr Glu
                               355                 360                 365

Glu Ile Ala Val Gln Asn Trp Leu Ala Arg Val Gly Arg Glu Arg Leu
                               370                 375                 380

Ser Arg Met Ala Ile Ser Gly Asp Asp Cys Val Val Lys Pro Leu Asp
            385                 390                 395                 400

Asp Arg Phe Ala Ser Ala Leu Thr Ala Leu Asn Asp Met Gly Lys Val
                               405                 410                 415

Arg Lys Asp Ile Gln Gln Trp Glu Pro Ser Arg Gly Trp Asn Asp Trp
                               420                 425                 430

Thr Gln Val Pro Phe Cys Ser His His Phe His Glu Leu Ile Met Lys
                               435                 440                 445

Asp Gly Arg Val Leu Val Val Pro Cys Arg Asn Gln Asp Glu Leu Ile
                               450                 455                 460

Gly Arg Ala Arg Ile Ser Gln Gly Ala Gly Trp Ser Leu Arg Glu Thr
            465                 470                 475                 480

Ala Cys Leu Gly Lys Ser Tyr Ala Gln Met Trp Ser Leu Met Tyr Phe
                               485                 490                 495
```

```
His Arg Arg Asp Leu Arg Leu Ala Ala Asn Ala Ile Cys Ser Ala Val
            500                 505                 510

Pro Ser His Trp Val Pro Thr Ser Arg Thr Thr Trp Ser Ile His Ala
            515                 520                 525

Lys His Glu Trp Met Thr Thr Glu Asp Met Leu Thr Val Trp Asn Arg
530                 535                 540

Val Trp Ile Gln Glu Asn Pro Trp Met Glu Asp Lys Thr Pro Val Glu
545                 550                 555                 560

Ser Trp Glu Glu Ile Pro Tyr Leu Gly Lys Arg Glu Asp Gln Trp Cys
                565                 570                 575

Gly Ser Leu Ile Gly Leu Thr Ser Arg Ala Thr Trp Ala Lys Asn Ile
            580                 585                 590

Gln Thr Ala Ile Asn Gln Val Arg Ser Leu Ile Gly Asn Glu Glu Tyr
            595                 600                 605

Thr Asp Tyr Met Pro Ser Met Lys Arg Phe Arg Lys Glu Glu Glu Glu
            610                 615                 620

Ala Gly Val Leu Trp
625

<210> SEQ ID NO 17
<211> LENGTH: 630
<212> TYPE: PRT
<213> ORGANISM: Flavivirus sp.
<220> FEATURE:
<221> NAME/KEY: misc_feature
<223> OTHER INFORMATION: Dengue3

<400> SEQUENCE: 17

Pro Asn Met Asp Val Ile Gly Glu Arg Ile Lys Arg Ile Lys Glu Glu
1               5                   10                  15

His Ser Ser Thr Trp His Tyr Asp Asp Glu Asn Pro Tyr Lys Thr Trp
            20                  25                  30

Ala Tyr His Gly Ser Tyr Glu Val Lys Ala Thr Gly Ser Ala Ser Ser
            35                  40                  45

Met Ile Asn Gly Val Val Lys Leu Leu Thr Lys Pro Trp Asp Val Val
50                  55                  60

Pro Met Val Thr Gln Met Ala Met Thr Asp Thr Thr Pro Phe Gly Gln
65                  70                  75                  80

Gln Arg Val Phe Lys Glu Lys Val Asp Thr Arg Thr Pro Arg Pro Met
                85                  90                  95

Pro Gly Thr Arg Lys Val Met Glu Ile Thr Ala Glu Trp Leu Trp Arg
            100                 105                 110

Thr Leu Gly Arg Asn Lys Arg Pro Arg Leu Cys Thr Arg Glu Glu Phe
            115                 120                 125

Thr Lys Lys Val Arg Thr Asn Ala Ala Met Gly Ala Val Phe Thr Glu
130                 135                 140

Glu Asn Gln Trp Asp Ser Ala Arg Ala Ala Val Glu Asp Glu Glu Phe
145                 150                 155                 160

Trp Lys Leu Val Asp Arg Glu Arg Glu Leu His Lys Leu Gly Lys Cys
                165                 170                 175

Gly Ser Cys Val Tyr Asn Met Met Gly Lys Arg Glu Lys Lys Leu Gly
            180                 185                 190

Glu Phe Gly Lys Ala Lys Gly Ser Arg Ala Ile Trp Tyr Met Trp Leu
            195                 200                 205

Gly Ala Arg Tyr Leu Glu Phe Glu Ala Leu Gly Phe Leu Asn Glu Asp
210                 215                 220
```

-continued

His Trp Phe Ser Arg Glu Asn Ser Tyr Ser Gly Val Glu Gly Glu Gly
225                 230                 235                 240

Leu His Lys Leu Gly Tyr Ile Leu Arg Asp Ile Ser Lys Ile Pro Gly
            245                 250                 255

Gly Ala Met Tyr Ala Asp Asp Thr Ala Gly Trp Asp Thr Arg Ile Thr
        260                 265                 270

Glu Asp Asp Leu His Asn Glu Glu Lys Ile Thr Gln Gln Met Asp Pro
    275                 280                 285

Glu His Arg Gln Leu Ala Asn Ala Ile Phe Lys Leu Thr Tyr Gln Asn
290                 295                 300

Lys Val Val Lys Val Gln Arg Pro Thr Pro Lys Gly Thr Val Met Asp
305                 310                 315                 320

Ile Ile Ser Arg Lys Asp Gln Arg Gly Ser Gly Gln Val Gly Thr Tyr
                325                 330                 335

Gly Leu Asn Thr Phe Thr Asn Met Glu Ala Gln Leu Ile Arg Gln Met
            340                 345                 350

Glu Gly Glu Gly Val Leu Ser Lys Ala Asp Leu Glu Asn Pro His Pro
        355                 360                 365

Leu Glu Lys Lys Ile Thr Gln Trp Leu Glu Thr Lys Gly Val Glu Arg
    370                 375                 380

Leu Lys Arg Met Ala Ile Ser Gly Asp Asp Cys Val Val Lys Pro Ile
385                 390                 395                 400

Asp Asp Arg Phe Ala Asn Ala Leu Leu Ala Leu Asn Asp Met Gly Lys
                405                 410                 415

Val Arg Lys Asp Ile Pro Gln Trp Gln Pro Ser Lys Gly Trp His Asp
            420                 425                 430

Trp Gln Gln Val Pro Phe Cys Ser His His Phe His Glu Leu Ile Met
    435                 440                 445

Lys Asp Gly Arg Lys Leu Val Val Pro Cys Arg Pro Gln Asp Glu Leu
450                 455                 460

Ile Gly Arg Ala Arg Ile Ser Gln Gly Ala Gly Trp Ser Leu Arg Glu
465                 470                 475                 480

Thr Ala Cys Leu Gly Lys Ala Tyr Ala Gln Met Trp Thr Leu Met Tyr
                485                 490                 495

Phe His Arg Arg Asp Leu Arg Leu Ala Ser Asn Ala Ile Cys Ser Ala
            500                 505                 510

Val Pro Val His Trp Val Pro Thr Ser Arg Thr Thr Trp Ser Ile His
    515                 520                 525

Ala His His Gln Trp Met Thr Thr Glu Asp Met Leu Thr Val Trp Asn
530                 535                 540

Arg Val Trp Ile Glu Asp Asn Pro Trp Met Glu Asp Lys Thr Pro Ile
545                 550                 555                 560

Thr Thr Trp Glu Asp Val Pro Tyr Leu Gly Lys Arg Glu Asp Gln Trp
                565                 570                 575

Cys Gly Ser Leu Ile Gly Leu Thr Ser Arg Ala Thr Trp Ala Gln Asn
            580                 585                 590

Ile Leu Thr Ala Ile Gln Gln Val Arg Ser Leu Ile Gly Asn Glu Glu
    595                 600                 605

Phe Leu Asp Tyr Met Pro Ser Met Lys Arg Phe Arg Lys Glu Glu Glu
610                 615                 620

Ser Glu Gly Ala Ile Trp
625                 630

<210> SEQ ID NO 18

```
<211> LENGTH: 629
<212> TYPE: PRT
<213> ORGANISM: Flavivirus sp.
<220> FEATURE:
<221> NAME/KEY: misc_feature
<223> OTHER INFORMATION: Dengue1

<400> SEQUENCE: 18
```

| | | | | | | | | | | | | | | |
|---|---|---|---|---|---|---|---|---|---|---|---|---|---|---|
|Ala|Asn|Leu|Asp|Ile|Ile|Gly|Gln|Arg|Ile|Glu|Asn|Ile|Lys|Asn|Glu|
|1| | |5| | | | |10| | | | |15| | |
|His|Lys|Ser|Thr|Trp|His|Tyr|Asp|Glu|Asp|Asn|Pro|Tyr|Lys|Thr|Trp|
| | | |20| | | |25| | | |30| | | | |
|Ala|Tyr|His|Gly|Ser|Tyr|Glu|Val|Lys|Pro|Ser|Gly|Ser|Ala|Ser|Ser|
| | |35| | | |40| | | |45| | | | | |
|Met|Val|Asn|Gly|Val|Val|Arg|Leu|Leu|Thr|Lys|Pro|Trp|Asp|Val|Ile|
|50| | | |55| | | | |60| | | | | | |
|Pro|Met|Val|Thr|Gln|Ile|Ala|Met|Thr|Asp|Thr|Thr|Pro|Phe|Gly|Gln|
|65| | | |70| | | |75| | | | |80| | |
|Gln|Arg|Val|Phe|Lys|Glu|Lys|Val|Asp|Thr|Arg|Thr|Pro|Lys|Ala|Lys|
| | | | |85| | | |90| | | | |95| | |
|Arg|Gly|Thr|Ala|Gln|Ile|Met|Glu|Val|Thr|Ala|Arg|Trp|Leu|Trp|Gly|
| | | |100| | | | |105| | | |110| | | |
|Phe|Leu|Ser|Arg|Asn|Lys|Lys|Pro|Arg|Ile|Cys|Thr|Arg|Glu|Glu|Phe|
| | | |115| | | | |120| | | |125| | | |
|Thr|Arg|Lys|Val|Arg|Ser|Asn|Ala|Ala|Ile|Gly|Ala|Val|Phe|Val|Asp|
|130| | | | |135| | | | |140| | | | | |
|Glu|Asn|Gln|Trp|Asn|Ser|Ala|Lys|Glu|Ala|Val|Ala|Asp|Glu|Arg|Phe|
|145| | | | |150| | | | |155| | | | |160|
|Trp|Asp|Leu|Val|His|Lys|Glu|Arg|Glu|Leu|His|Lys|Gln|Gly|Lys|Cys|
| | | | |165| | | | |170| | | | |175| |
|Ala|Thr|Cys|Val|Tyr|Asn|Met|Met|Gly|Lys|Arg|Glu|Lys|Lys|Leu|Gly|
| | | |180| | | | |185| | | | |190| | |
|Glu|Phe|Gly|Lys|Ala|Lys|Gly|Ser|Arg|Ala|Ile|Trp|Tyr|Met|Trp|Leu|
| | |195| | | | |200| | | | |205| | | |
|Gly|Ala|Arg|Phe|Leu|Glu|Phe|Glu|Ala|Leu|Gly|Phe|Met|Asn|Glu|Asp|
| |210| | | | |215| | | | |220| | | | |
|His|Trp|Phe|Ser|Arg|Glu|Asn|Ser|Leu|Ser|Gly|Val|Glu|Gly|Glu|Gly|
|225| | | | |230| | | | |235| | | | |240|
|Leu|His|Lys|Leu|Gly|Tyr|Ile|Leu|Arg|Asp|Ile|Ser|Lys|Ile|Pro|Gly|
| | | | |245| | | | |250| | | | |255| |
|Gly|Asn|Met|Tyr|Ala|Asp|Asp|Thr|Ala|Gly|Trp|Asp|Thr|Arg|Ile|Thr|
| | | |260| | | | |265| | | | |270| | |
|Glu|Asp|Asp|Leu|Gln|Asn|Glu|Ala|Lys|Ile|Thr|Asp|Ile|Met|Glu|Pro|
| | |275| | | | |280| | | | |285| | | |
|Glu|His|Ala|Leu|Leu|Ala|Thr|Ser|Ile|Phe|Lys|Leu|Thr|Tyr|Gln|Asn|
| |290| | | | |295| | | | |300| | | | |
|Lys|Val|Val|Arg|Val|Gln|Arg|Pro|Ala|Lys|Asn|Gly|Thr|Val|Met|Asp|
|305| | | | |310| | | | |315| | | | |320|
|Val|Ile|Ser|Arg|Arg|Asp|Gln|Arg|Gly|Ser|Gly|Gln|Val|Gly|Thr|Tyr|
| | | | |325| | | | |330| | | | |335| |
|Gly|Leu|Asn|Thr|Phe|Thr|Asn|Met|Glu|Ala|Gln|Leu|Ile|Arg|Gln|Met|
| | | |340| | | | |345| | | | |350| | |
|Glu|Ser|Glu|Gly|Ile|Phe|Ser|Pro|Ser|Glu|Leu|Glu|Thr|Pro|Asn|Leu|
| | |355| | | | |360| | | | |365| | | |
|Ala|Glu|Arg|Val|Leu|Asp|Trp|Leu|Glu|Lys|His|Gly|Val|Glu|Arg|Leu|
| |370| | | | |375| | | | |380| | | | |

Lys Arg Met Ala Ile Ser Gly Asp Asp Cys Val Val Lys Pro Ile Asp
385                 390                 395                 400

Asp Arg Phe Ala Thr Ala Leu Thr Ala Leu Asn Asp Met Gly Lys Val
            405                 410                 415

Arg Lys Asp Ile Pro Gln Trp Glu Pro Ser Lys Gly Trp Asn Asp Trp
        420                 425                 430

Gln Gln Val Pro Phe Cys Ser His His Phe His Gln Leu Ile Met Lys
    435                 440                 445

Asp Gly Arg Glu Ile Val Val Pro Cys Arg Asn Gln Asp Glu Leu Val
450                 455                 460

Gly Arg Ala Arg Val Ser Gln Gly Ala Gly Trp Ser Leu Arg Glu Thr
465                 470                 475                 480

Ala Cys Leu Gly Lys Ser Tyr Ala Gln Met Trp Gln Leu Met Tyr Phe
                485                 490                 495

His Arg Arg Asp Leu Arg Leu Ala Ala Asn Ala Ile Cys Ser Ala Val
            500                 505                 510

Pro Val Asp Trp Val Pro Thr Ser Arg Thr Thr Trp Ser Ile His Ala
        515                 520                 525

His His Gln Trp Met Thr Thr Glu Asp Met Leu Ser Val Trp Asn Arg
    530                 535                 540

Val Trp Ile Glu Glu Asn Pro Trp Met Glu Asp Lys Thr His Val Ser
545                 550                 555                 560

Ser Trp Glu Asp Val Pro Tyr Leu Gly Lys Arg Glu Asp Gln Trp Cys
                565                 570                 575

Gly Ser Leu Ile Gly Leu Thr Ala Arg Ala Thr Trp Ala Thr Asn Ile
            580                 585                 590

Gln Val Ala Ile Asn Gln Val Arg Arg Leu Ile Gly Asn Glu Asn Tyr
        595                 600                 605

Leu Asp Tyr Met Thr Ser Met Lys Arg Phe Lys Asn Glu Ser Asp Pro
    610                 615                 620

Glu Gly Ala Leu Trp
625

<210> SEQ ID NO 19
<211> LENGTH: 629
<212> TYPE: PRT
<213> ORGANISM: Flavivirus sp.
<220> FEATURE:
<221> NAME/KEY: misc_feature
<223> OTHER INFORMATION: Dengue4

<400> SEQUENCE: 19

Pro Asp Met Thr Ile Ile Gly Arg Arg Leu Gln Arg Leu Gln Glu Glu
1               5                   10                  15

His Lys Glu Thr Trp His Tyr Asp Gln Glu Asn Pro Tyr Arg Thr Trp
            20                  25                  30

Ala Tyr His Gly Ser Tyr Glu Ala Pro Ser Thr Gly Ser Ala Ser Ser
        35                  40                  45

Met Val Asn Gly Val Val Lys Leu Leu Thr Lys Pro Trp Asp Val Ile
    50                  55                  60

Pro Met Val Thr Gln Leu Ala Met Thr Asp Thr Thr Pro Phe Gly Gln
65                  70                  75                  80

Gln Arg Val Phe Lys Glu Lys Val Asp Thr Arg Thr Pro Gln Pro Lys
                85                  90                  95

Pro Gly Thr Arg Met Val Met Thr Thr Thr Ala Asn Trp Leu Trp Ala
            100                 105                 110

-continued

```
Leu Leu Gly Lys Lys Lys Asn Pro Arg Leu Cys Thr Arg Glu Glu Phe
            115                 120                 125
Ile Ser Lys Val Arg Ser Asn Ala Ala Ile Gly Ala Val Phe Gln Glu
        130                 135                 140
Glu Gln Gly Trp Thr Ser Ala Ser Glu Ala Val Asn Asp Ser Arg Phe
145                 150                 155                 160
Trp Glu Leu Val Asp Lys Glu Arg Ala Leu His Gln Glu Gly Lys Cys
                165                 170                 175
Glu Ser Cys Val Tyr Asn Met Met Gly Lys Arg Glu Lys Lys Leu Gly
            180                 185                 190
Glu Phe Gly Arg Ala Lys Gly Ser Arg Ala Ile Trp Tyr Met Trp Leu
        195                 200                 205
Gly Ala Arg Phe Leu Glu Phe Glu Ala Leu Gly Phe Leu Asn Glu Asp
    210                 215                 220
His Trp Phe Gly Arg Glu Asn Ser Trp Ser Gly Val Glu Gly Glu Gly
225                 230                 235                 240
Leu His Arg Leu Gly Tyr Ile Leu Glu Glu Ile Asp Lys Lys Asp Gly
                245                 250                 255
Asp Leu Met Tyr Ala Asp Asp Thr Ala Gly Trp Asp Thr Arg Ile Thr
            260                 265                 270
Glu Asp Asp Leu Gln Asn Glu Glu Leu Ile Thr Glu Gln Met Ala Pro
        275                 280                 285
His His Lys Ile Leu Ala Lys Ala Ile Phe Lys Leu Thr Tyr Gln Asn
    290                 295                 300
Lys Val Val Lys Val Leu Arg Pro Thr Pro Arg Gly Ala Val Met Asp
305                 310                 315                 320
Ile Ile Ser Arg Lys Asp Gln Arg Gly Ser Gly Gln Val Gly Thr Tyr
                325                 330                 335
Gly Leu Asn Thr Phe Thr Asn Met Glu Val Gln Leu Ile Arg Gln Met
            340                 345                 350
Glu Ala Glu Gly Val Ile Thr Gln Asp Asp Met Gln Asn Pro Lys Gly
        355                 360                 365
Leu Lys Glu Arg Val Glu Lys Trp Leu Lys Glu Cys Gly Val Asp Arg
    370                 375                 380
Leu Lys Arg Met Ala Ile Ser Gly Asp Asp Cys Val Val Lys Pro Leu
385                 390                 395                 400
Asp Glu Arg Phe Gly Thr Ser Leu Leu Phe Leu Asn Asp Met Gly Lys
                405                 410                 415
Val Arg Lys Asp Ile Pro Gln Trp Glu Pro Ser Lys Gly Trp Lys Asn
            420                 425                 430
Trp Gln Glu Val Pro Phe Cys Ser His His Phe His Lys Ile Phe Met
        435                 440                 445
Lys Asp Gly Arg Ser Leu Val Val Pro Cys Arg Asn Gln Asp Glu Leu
    450                 455                 460
Ile Gly Arg Ala Arg Ile Ser Gln Gly Ala Gly Trp Ser Leu Arg Glu
465                 470                 475                 480
Thr Ala Cys Leu Gly Lys Ala Tyr Ala Gln Met Trp Ser Leu Met Tyr
                485                 490                 495
Phe His Arg Arg Asp Leu Arg Leu Ala Ser Met Ala Ile Cys Ser Ala
            500                 505                 510
Val Pro Thr Glu Trp Phe Pro Thr Ser Arg Thr Thr Trp Ser Ile His
        515                 520                 525
Ala His His Gln Trp Met Thr Thr Glu Asp Met Leu Lys Val Trp Asn
```

```
                      530                 535                 540
Arg Val Trp Ile Glu Asp Asn Pro Asn Met Thr Asp Lys Thr Pro Val
545                 550                 555                 560

His Ser Trp Glu Asp Ile Pro Tyr Leu Gly Lys Arg Glu Asp Leu Trp
                565                 570                 575

Cys Gly Ser Leu Ile Gly Leu Ser Ser Arg Ala Thr Trp Ala Lys Asn
                580                 585                 590

Ile His Thr Ala Ile Thr Gln Val Arg Asn Leu Ile Gly Lys Glu Glu
                595                 600                 605

Tyr Val Asp Tyr Met Pro Val Met Lys Arg Tyr Ser Ala Pro Ser Glu
                610                 615                 620

Ser Glu Gly Val Leu
625

<210> SEQ ID NO 20
<211> LENGTH: 632
<212> TYPE: PRT
<213> ORGANISM: Flavivirus sp.
<220> FEATURE:
<221> NAME/KEY: misc_feature
<223> OTHER INFORMATION: West Nile

<400> SEQUENCE: 20

Ser Asp Thr Ser Lys Ile Asn Asn Arg Ile Glu Arg Leu Arg Arg Glu
1               5                   10                  15

Tyr Ser Ser Thr Trp His His Asp Glu Asn His Pro Tyr Arg Thr Trp
                20                  25                  30

Asn Tyr His Gly Ser Tyr Asp Val Lys Pro Thr Gly Ser Ala Ser Ser
                35                  40                  45

Leu Val Asn Gly Val Val Arg Leu Leu Ser Lys Pro

```
                260                 265                 270
Arg Ala Asp Leu Glu Asn Glu Ala Lys Val Leu Glu Leu Leu Asp Gly
        275                 280                 285

Glu His Arg Arg Leu Ala Arg Ala Ile Ile Glu Leu Thr Tyr Arg His
        290                 295                 300

Lys Val Val Lys Val Met Arg Pro Ala Ala Asp Gly Arg Thr Val Met
305                 310                 315                 320

Asp Val Ile Ser Arg Glu Asp Gln Arg Gly Ser Gly Gln Val Val Thr
                325                 330                 335

Tyr Ala Leu Asn Thr Phe Thr Asn Leu Ala Val Gln Leu Val Arg Met
                340                 345                 350

Met Glu Gly Glu Gly Val Ile Gly Pro Asp Asp Val Glu Lys Leu Thr
                355                 360                 365

Lys Gly Lys Gly Pro Lys Val Arg Thr Trp Leu Phe Glu Asn Gly Glu
        370                 375                 380

Glu Arg Leu Ser Arg Met Ala Val Ser Gly Asp Asp Cys Val Val Lys
385                 390                 395                 400

Pro Leu Asp Asp Arg Phe Ala Thr Ser Leu His Phe Leu Asn Ala Met
                405                 410                 415

Ser Lys Val Arg Lys Asp Ile Gln Glu Trp Lys Pro Ser Thr Gly Trp
                420                 425                 430

Tyr Asp Trp Gln Gln Val Pro Phe Cys Ser Asn His Phe Thr Glu Leu
        435                 440                 445

Ile Met Lys Asp Gly Arg Thr Leu Val Val Pro Cys Arg Gly Gln Asp
        450                 455                 460

Glu Leu Val Gly Arg Ala Arg Ile Ser Pro Gly Ala Gly Trp Asn Val
465                 470                 475                 480

Arg Asp Thr Ala Cys Leu Ala Lys Ser Tyr Ala Gln Met Trp Leu Leu
                485                 490                 495

Leu Tyr Phe His Arg Arg Asp Leu Arg Leu Met Ala Asn Ala Ile Cys
                500                 505                 510

Ser Ala Val Pro Val Asn Trp Val Pro Thr Gly Arg Thr Thr Trp Ser
        515                 520                 525

Ile His Ala Gly Gly Glu Trp Met Thr Thr Glu Asp Met Leu Glu Val
        530                 535                 540

Trp Asn Arg Val Trp Ile Glu Glu Asn Glu Trp Met Glu Asp Lys Thr
545                 550                 555                 560

Pro Val Glu Lys Trp Ser Asp Val Pro Tyr Ser Gly Lys Arg Glu Asp
                565                 570                 575

Ile Trp Cys Gly Ser Leu Ile Gly Thr Arg Ala Arg Ala Thr Trp Ala
                580                 585                 590

Glu Asn Ile Gln Val Ala Ile Asn Gln Val Arg Ala Ile Ile Gly Asp
        595                 600                 605

Glu Lys Tyr Val Asp Tyr Met Ser Ser Leu Lys Arg Tyr Glu Asp Thr
        610                 615                 620

Thr Leu Val Glu Asp Thr Val Leu
625                 630

<210> SEQ ID NO 21
<211> LENGTH: 632
<212> TYPE: PRT
<213> ORGANISM: Flavivirus sp.
<220> FEATURE:
<221> NAME/KEY: misc_feature
<223> OTHER INFORMATION: Kunjin
```

<400> SEQUENCE: 21

| Ser | Asp | Thr | Ser | Lys | Ile | Lys | Asn | Arg | Ile | Glu | Arg | Leu | Arg | Arg | Glu |
|---|---|---|---|---|---|---|---|---|---|---|---|---|---|---|---|
| 1 | | | | 5 | | | | | 10 | | | | | 15 | |

| Tyr | Ser | Ser | Thr | Trp | His | His | Asp | Glu | Asn | His | Pro | Tyr | Arg | Thr | Trp |
|---|---|---|---|---|---|---|---|---|---|---|---|---|---|---|---|
| | | | 20 | | | | | 25 | | | | | 30 | | |

| Asn | Tyr | His | Gly | Ser | Tyr | Glu | Val | Lys | Pro | Thr | Gly | Ser | Ala | Ser | Ser |
|---|---|---|---|---|---|---|---|---|---|---|---|---|---|---|---|
| | | | | 35 | | | | | 40 | | | | | 45 | |

| Leu | Val | Asn | Gly | Val | Val | Arg | Leu | Leu | Ser | Lys | Pro | Trp | Asp | Thr | Ile |
|---|---|---|---|---|---|---|---|---|---|---|---|---|---|---|---|
| | | 50 | | | | | 55 | | | | | 60 | | | |

| Thr | Asn | Val | Thr | Thr | Met | Ala | Met | Thr | Asp | Thr | Thr | Pro | Phe | Gly | Gln |
|---|---|---|---|---|---|---|---|---|---|---|---|---|---|---|---|
| 65 | | | | | 70 | | | | | 75 | | | | | 80 |

| Gln | Arg | Val | Phe | Lys | Glu | Lys | Val | Asp | Thr | Lys | Ala | Pro | Glu | Pro | Pro |
|---|---|---|---|---|---|---|---|---|---|---|---|---|---|---|---|
| | | | | 85 | | | | | 90 | | | | | 95 | |

| Glu | Gly | Val | Lys | Tyr | Val | Leu | Asn | Glu | Thr | Thr | Asn | Trp | Leu | Trp | Ala |
|---|---|---|---|---|---|---|---|---|---|---|---|---|---|---|---|
| | | | 100 | | | | | 105 | | | | | 110 | | |

| Phe | Leu | Ala | Arg | Glu | Lys | Arg | Pro | Arg | Met | Cys | Ser | Arg | Glu | Glu | Phe |
|---|---|---|---|---|---|---|---|---|---|---|---|---|---|---|---|
| | | | 115 | | | | | 120 | | | | | 125 | | |

| Ile | Arg | Lys | Val | Asn | Ser | Asn | Ala | Ala | Leu | Gly | Ala | Met | Phe | Glu | Glu |
|---|---|---|---|---|---|---|---|---|---|---|---|---|---|---|---|
| | 130 | | | | | 135 | | | | | 140 | | | | |

| Gln | Asn | Gln | Trp | Arg | Ser | Ala | Arg | Glu | Ala | Val | Glu | Asp | Pro | Lys | Phe |
|---|---|---|---|---|---|---|---|---|---|---|---|---|---|---|---|
| 145 | | | | | 150 | | | | | 155 | | | | | 160 |

| Trp | Glu | Met | Val | Asp | Glu | Glu | Arg | Glu | Ala | His | Leu | Arg | Gly | Glu | Cys |
|---|---|---|---|---|---|---|---|---|---|---|---|---|---|---|---|
| | | | | 165 | | | | | 170 | | | | | 175 | |

| His | Thr | Cys | Ile | Tyr | Asn | Met | Met | Gly | Lys | Arg | Glu | Lys | Lys | Pro | Gly |
|---|---|---|---|---|---|---|---|---|---|---|---|---|---|---|---|
| | | | 180 | | | | | 185 | | | | | 190 | | |

| Glu | Phe | Gly | Lys | Ala | Lys | Gly | Ser | Arg | Ala | Ile | Trp | Phe | Met | Trp | Leu |
|---|---|---|---|---|---|---|---|---|---|---|---|---|---|---|---|
| | | 195 | | | | | 200 | | | | | 205 | | | |

| Gly | Ala | Arg | Phe | Leu | Glu | Phe | Glu | Ala | Leu | Gly | Phe | Leu | Asn | Glu | Asp |
|---|---|---|---|---|---|---|---|---|---|---|---|---|---|---|---|
| 210 | | | | | 215 | | | | | 220 | | | | | |

| His | Trp | Leu | Gly | Arg | Lys | Asn | Ser | Gly | Gly | Val | Glu | Gly | Leu | Gly | |
|---|---|---|---|---|---|---|---|---|---|---|---|---|---|---|---|
| 225 | | | | | 230 | | | | | 235 | | | | | 240 |

| Leu | Gln | Lys | Leu | Gly | Tyr | Ile | Leu | Arg | Glu | Val | Gly | Thr | Arg | Pro | Gly |
|---|---|---|---|---|---|---|---|---|---|---|---|---|---|---|---|
| | | | | 245 | | | | | 250 | | | | | 255 | |

| Gly | Arg | Ile | Tyr | Ala | Asp | Asp | Thr | Ala | Gly | Trp | Asp | Thr | Arg | Ile | Thr |
|---|---|---|---|---|---|---|---|---|---|---|---|---|---|---|---|
| | | | 260 | | | | | 265 | | | | | 270 | | |

| Arg | Ala | Asp | Leu | Glu | Asn | Glu | Ala | Lys | Val | Leu | Glu | Leu | Leu | Asp | Gly |
|---|---|---|---|---|---|---|---|---|---|---|---|---|---|---|---|
| | | 275 | | | | | 280 | | | | | 285 | | | |

| Glu | His | Arg | Arg | Leu | Ala | Arg | Ala | Ile | Ile | Glu | Leu | Thr | Tyr | Arg | His |
|---|---|---|---|---|---|---|---|---|---|---|---|---|---|---|---|
| | 290 | | | | | 295 | | | | | 300 | | | | |

| Lys | Val | Val | Lys | Val | Met | Arg | Pro | Ala | Ala | Asp | Gly | Arg | Thr | Val | Met |
|---|---|---|---|---|---|---|---|---|---|---|---|---|---|---|---|
| 305 | | | | | 310 | | | | | 315 | | | | | 320 |

| Asp | Val | Ile | Ser | Arg | Glu | Asp | Gln | Arg | Gly | Ser | Gly | Gln | Val | Val | Thr |
|---|---|---|---|---|---|---|---|---|---|---|---|---|---|---|---|
| | | | | 325 | | | | | 330 | | | | | 335 | |

| Tyr | Ala | Leu | Asn | Thr | Phe | Thr | Asn | Leu | Ala | Val | Gln | Leu | Val | Arg | Met |
|---|---|---|---|---|---|---|---|---|---|---|---|---|---|---|---|
| | | | 340 | | | | | 345 | | | | | 350 | | |

| Met | Glu | Gly | Glu | Gly | Val | Ile | Gly | Pro | Asp | Asp | Val | Glu | Lys | Leu | Thr |
|---|---|---|---|---|---|---|---|---|---|---|---|---|---|---|---|
| | | 355 | | | | | 360 | | | | | 365 | | | |

| Lys | Gly | Lys | Gly | Pro | Lys | Val | Arg | Thr | Trp | Leu | Ser | Glu | Asn | Gly | Glu |
|---|---|---|---|---|---|---|---|---|---|---|---|---|---|---|---|
| 370 | | | | | 375 | | | | | 380 | | | | | |

| Glu | Arg | Leu | Ser | Arg | Met | Ala | Val | Ser | Gly | Asp | Asp | Cys | Val | Val | Lys |
|---|---|---|---|---|---|---|---|---|---|---|---|---|---|---|---|
| 385 | | | | | 390 | | | | | 395 | | | | | 400 |

| Pro | Leu | Asp | Asp | Arg | Phe | Ala | Thr | Ser | Leu | His | Phe | Leu | Asn | Ala | Met |
|---|---|---|---|---|---|---|---|---|---|---|---|---|---|---|---|
| | | | | 405 | | | | | 410 | | | | | 415 | |

Ser Lys Val Arg Lys Asp Ile Gln Glu Trp Lys Pro Ser Thr Gly Trp
            420                 425                 430

Tyr Asp Trp Gln Gln Val Pro Phe Cys Ser Asn His Phe Thr Glu Leu
            435                 440                 445

Ile Met Lys Asp Gly Arg Thr Leu Val Thr Pro Cys Arg Gly Gln Asp
450                 455                 460

Glu Leu Val Gly Arg Ala Arg Ile Ser Pro Gly Ala Gly Trp Asn Val
465                 470                 475                 480

Arg Asp Thr Ala Cys Leu Ala Lys Ser Tyr Ala Gln Met Trp Leu Leu
                485                 490                 495

Leu Tyr Phe His Arg Arg Asp Leu Arg Leu Met Ala Asn Ala Ile Cys
            500                 505                 510

Ser Ala Val Pro Val Asn Trp Val Pro Thr Gly Arg Thr Thr Trp Ser
            515                 520                 525

Ile His Ala Gly Gly Glu Trp Met Thr Thr Glu Asp Met Leu Glu Val
    530                 535                 540

Trp Asn Arg Val Trp Ile Glu Glu Asn Glu Trp Met Glu Asp Lys Thr
545                 550                 555                 560

Pro Val Glu Lys Trp Ser Asp Val Pro Tyr Ser Gly Lys Arg Glu Asp
                565                 570                 575

Ile Trp Cys Gly Ser Leu Ile Gly Thr Arg Ala Arg Ala Thr Trp Ala
            580                 585                 590

Glu Asn Ile Gln Val Ala Ile Asn Gln Val Arg Ser Ile Ile Gly Asp
            595                 600                 605

Glu Lys Tyr Val Asp Tyr Met Ser Ser Leu Lys Arg Tyr Glu Asp Thr
    610                 615                 620

Thr Leu Val Glu Asp Thr Val Leu
625                 630

<210> SEQ ID NO 22
<211> LENGTH: 632
<212> TYPE: PRT
<213> ORGANISM: Flavivirus sp.

```
Gln Asn Gln Trp Ser Thr Ala Arg Glu Ala Val Asp Asp Pro Arg Phe
145                 150                 155                 160

Trp Glu Met Val Asp Glu Arg Glu Asn His Leu Arg Gly Glu Cys
            165                 170                 175

His Thr Cys Ile Tyr Asn Met Met Gly Lys Arg Glu Lys Lys Pro Gly
            180                 185                 190

Glu Phe Gly Lys Ala Lys Gly Ser Arg Ala Ile Trp Phe Met Trp Leu
        195                 200                 205

Gly Ala Arg Tyr Leu Glu Phe Glu Ala Leu Gly Phe Leu Asn Glu Asp
        210                 215                 220

His Trp Leu Ser Arg Glu Asn Ser Gly Gly Val Glu Gly Ser Gly
225                 230                 235                 240

Val Gln Lys Leu Gly Tyr Ile Leu Arg Asp Ile Ala Gly Lys Gln Gly
                245                 250                 255

Gly Lys Met Tyr Ala Asp Asp Thr Ala Gly Trp Asp Thr Arg Ile Thr
            260                 265                 270

Arg Thr Asp Leu Glu Asn Glu Ala Lys Val Leu Glu Leu Leu Asp Gly
        275                 280                 285

Glu His Arg Met Leu Ala Arg Ala Ile Ile Glu Leu Thr Tyr Arg His
    290                 295                 300

Lys Val Val Lys Val Met Arg Pro Ala Ala Glu Gly Lys Thr Val Met
305                 310                 315                 320

Asp Val Ile Ser Arg Glu Asp Gln Arg Gly Ser Gly Gln Val Val Thr
                325                 330                 335

Tyr Ala Leu Asn Thr Phe Thr Asn Ile Ala Val Gln Leu Val Arg Leu
            340                 345                 350

Met Glu Ala Glu Gly Val Ile Gly Pro Gln His Leu Glu Gln Leu Pro
        355                 360                 365

Arg Lys Asn Lys Ile Ala Val Arg Thr Trp Leu Phe Glu Asn Gly Glu
370                 375                 380

Glu Arg Val Thr Arg Met Ala Ile Ser Gly Asp Asp Cys Val Val Lys
385                 390                 395                 400

Pro Leu Asp Asp Arg Phe Ala Thr Ala Leu His Phe Leu Asn Ala Met
                405                 410                 415

Ser Lys Val Arg Lys Asp Ile Gln Glu Trp Lys Pro Ser His Gly Trp
            420                 425                 430

His Asp Trp Gln Gln Val Pro Phe Cys Ser Asn His Phe Gln Glu Ile
        435                 440                 445

Val Met Lys Asp Gly Arg Ser Ile Val Val Pro Cys Arg Gly Gln Asp
        450                 455                 460

Glu Leu Ile Gly Arg Ala Arg Ile Ser Pro Gly Ala Gly Trp Asn Val
465                 470                 475                 480

Lys Asp Thr Ala Cys Leu Ala Lys Ala Tyr Ala Gln Met Trp Leu Leu
                485                 490                 495

Leu Tyr Phe His Arg Arg Asp Leu Arg Leu Met Ala Asn Ala Ile Cys
            500                 505                 510

Ser Ala Val Pro Val Asp Trp Val Pro Thr Gly Arg Thr Ser Trp Ser
        515                 520                 525

Ile His Ser Lys Gly Glu Trp Met Thr Thr Glu Asp Met Leu Gln Val
        530                 535                 540

Trp Asn Arg Val Trp Ile Glu Glu Asn Glu Trp Met Met Asp Lys Thr
545                 550                 555                 560

Pro Ile Thr Ser Trp Thr Asp Val Pro Tyr Val Gly Lys Arg Glu Asp
                565                 570                 575
```

-continued

```
Ile Trp Cys Gly Ser Leu Ile Gly Thr Arg Ser Arg Ala Thr Trp Ala
                580                 585                 590

Glu Asn Ile Tyr Ala Ala Ile Asn Gln Val Arg Ala Val Ile Gly Lys
            595                 600                 605

Glu Asn Tyr Val Asp Tyr Met Thr Ser Leu Arg Arg Tyr Glu Asp Val
        610                 615                 620

Leu Ile Gln Glu Asp Arg Val Ile
625                 630

<210> SEQ ID NO 23
<211> LENGTH: 633
<212> TYPE: PRT
<213> ORGANISM: Flavivirus sp.
<220> FEATURE:
<221> NAME/KEY: misc_feature
<223> OTHER INFORMATION: Yellow Fever

<400> SEQUENCE: 23

Leu Asp Lys Glu Ala Ile Glu Glu Arg Val Glu Arg Ile Lys Ser Glu
1               5                   10                  15

Tyr Met Thr Ser Trp Phe Tyr Asp Asn Asp Asn Pro Tyr Arg Thr Trp
            20                  25                  30

His Tyr Cys Gly Ser Tyr Val Thr Lys Thr Ser Gly Ser Ala Ala Ser
        35                  40                  45

Met Val Asn Gly Val Ile Lys Ile Leu Thr Tyr Pro Trp Asp Lys Ile
    50                  55                  60

Glu Glu Val Thr Arg Met

-continued

Lys Val Lys Val Leu Arg Pro Ala Pro Gly Gly Lys Ala Tyr Met
305                 310                 315                 320

Asp Val Ile Ser Arg Arg Asp Gln Arg Gly Ser Gly Gln Val Val Thr
            325                 330                 335

Tyr Ala Leu Asn Thr Ile Thr Asn Leu Lys Val Gln Leu Ile Arg Met
        340                 345                 350

Ala Glu Ala Glu Met Val Ile His His Gln His Val Gln Asp Cys Asp
    355                 360                 365

Glu Ser Val Leu Thr Arg Leu Glu Ala Trp Leu Thr Glu His Gly Cys
370                 375                 380

Asn Arg Leu Arg Arg Met Ala Val Ser Gly Asp Asp Cys Val Val Arg
385                 390                 395                 400

Pro Ile Asp Asp Arg Phe Gly Leu Ala Leu Ser His Leu Asn Ala Met
                405                 410                 415

Ser Lys Val Arg Lys Asp Ile Ser Glu Trp Gln Pro Ser Lys Gly Trp
            420                 425                 430

Asn Asp Trp Glu Asn Val Pro Phe Cys Ser His His Phe His Glu Leu
        435                 440                 445

Gln Leu Lys Asp Gly Arg Arg Ile Val Val Pro Cys Arg Glu Gln Asp
    450                 455                 460

Glu Leu Ile Gly Arg Gly Arg Val Ser Pro Gly Asn Gly Trp Met Ile
465                 470                 475                 480

Lys Glu Thr Ala Cys Leu Ser Lys Ala Tyr Ala Asn Met Trp Ser Leu
                485                 490                 495

Met Tyr Phe His Lys Arg Asp Met Arg Leu Leu Ser Leu Ala Val Ser
            500                 505                 510

Ser Ala Val Pro Thr Ser Trp Val Pro Gln Gly Arg Thr Thr Trp Ser
        515                 520                 525

Ile His Gly Lys Gly Glu Trp Met Thr Thr Glu Asp Met Leu Glu Val
    530                 535                 540

Trp Asn Arg Val Trp Ile Thr Asn Asn Pro His Met Gln Asp Lys Thr
545                 550                 555                 560

Met Val Lys Glu Trp Arg Asp Val Pro Tyr Leu Thr Lys Arg Gln Asp
                565                 570                 575

Lys Leu Cys Gly Ser Leu Ile Gly Met Thr Asn Arg Ala Thr Trp Ala
            580                 585                 590

Ser His Ile His Leu Val Ile His Arg Ile Arg Thr Leu Val Gly Gln
        595                 600                 605

Glu Lys Tyr Thr Asp Tyr Leu Thr Val Met Asp Arg Tyr Ser Val Asp
    610                 615                 620

Ala Asp Leu Gln Pro Gly Glu Leu Ile
625                 630

<210> SEQ ID NO 24
<211> LENGTH: 633
<212> TYPE: PRT
<213> ORGANISM: Flavivirus sp.
<220> FEATURE:
<221> NAME/KEY: misc_feature
<223> OTHER INFORMATION: Banzi

<400> SEQUENCE: 24

Leu Asp Leu Glu Lys Val Lys Ala Arg Ile Asn Arg Leu Lys Glu Glu
1               5                   10                  15

Gln Glu Ser Thr Trp Phe Val Asp Ser Asp His Pro Tyr Arg Thr Trp
            20                  25                  30

-continued

```
His Tyr His Gly Ser Tyr Val Ala Lys Gln Ser Gly Thr Ala Ala Ser
            35                  40                  45
Met Ile Asn Gly Val Val Lys Leu Leu Ser Gly Pro Trp Asp Arg Ile
 50                  55                  60
Glu Val Thr Asn Met Ala Met Thr Asp Thr Thr Pro Phe Gly Gln
 65                  70                  75                  80
Gln Arg Val Phe Lys Glu Lys Val Asp Thr Arg Ala Pro Glu Pro Pro
                 85                  90                  95
Gln Gly Thr Arg Glu Ile Met Lys Val Val Asn Gln Trp Leu Phe Asp
                100                 105                 110
Tyr Leu Gly Arg Thr Lys Gln Pro Arg Ile Cys Thr Lys Glu Glu Phe
                115                 120                 125
Ile Asn Lys Val Arg Ser His Ala Ala Leu Gly Gly Ile Leu Thr Glu
                130                 135                 140
Gln Glu Gly Trp Ser Ser Ala Ala Glu Ala Val Ala Asp Pro Arg Phe
145                 150                 155                 160
Trp Ser Leu Val Asp Lys Glu Arg Gln Ala His Leu Glu Gly Arg Cys
                165                 170                 175
Glu Thr Cys Ile Tyr Asn Met Met Gly Lys Arg Glu Lys Lys Pro Ser
                180                 185                 190
Glu Phe Gly Arg Ala Lys Gly Ser Arg Ala Ile Trp Tyr Met Trp Leu
                195                 200                 205
Gly Ala Arg Phe Leu Glu Phe Glu Ala Leu Gly Phe Leu Asn Glu Asp
                210                 215                 220
His Trp Leu Gly Arg Glu Asn Ser Lys Ala Gly Val Glu Gly Ile Gly
225                 230                 235                 240
Leu Gln Tyr Leu Gly Tyr Val Val Glu Val Ala Arg Lys Gly Asn
                245                 250                 255
Gly Leu Val Tyr Ala Asp Asp Thr Ala Gly Trp Asp Thr Arg Ile Thr
                260                 265                 270
Glu Ala Asp Leu Glu Asp Glu Gln Tyr Ile Met Lys Arg Met Ser Ala
                275                 280                 285
Glu His Arg Gln Leu Ala Trp Ala Val Met Glu Leu Thr Tyr Arg Asn
                290                 295                 300
Lys Val Val Lys Val Pro Arg Pro Gly Pro Gly Gly Lys Ile Leu Met
305                 310                 315                 320
Asp Val Ile Ser Arg Arg Asp Gln Arg Gly Ser Gly Gln Val Val Thr
                325                 330                 335
Tyr Pro Leu Asn Thr Ala Thr Asn Met Lys Val Gln Leu Ile Arg Met
                340                 345                 350
Ala Glu Ala Glu Asn Val Ile Thr Arg Asn Asp Val Lys Val Ser
                355                 360                 365
Leu Ile Thr Leu Lys Glu Leu Gln Leu Trp Leu Glu Val Asn Gly Val
                370                 375                 380
Asn Arg Leu Glu Arg Met Ala Val Ser Gly Asp Asp Cys Ile Val Ala
385                 390                 395                 400
Pro Val Asp Glu Ser Phe Ala Gly Ala Leu His Leu Asn Ala Met
                405                 410                 415
Ser Lys Thr Arg Lys Asp Ile Ser Glu Trp Glu Asn Ser Arg Gly Trp
                420                 425                 430
Thr Asp Trp Glu Ser Val Pro Phe Cys Ser His His Phe His Thr Leu
                435                 440                 445
Tyr Leu Lys Asp Gly Arg Thr Ile Ile Ala Pro Cys Arg Cys Gln Asp
```

```
                    450                 455                 460
Glu Leu Ile Gly Arg Ala Arg Ile Ser Pro Gly Asn Gly Trp Met Ile
465                 470                 475                 480

Lys Glu Thr Ala Gly Leu Ser Lys Ala Tyr Ala Gln Met Trp Thr Leu
                    485                 490                 495

Met Tyr Phe His Arg Arg Asp Leu Arg Leu Met Ala Asn Ala Ile Cys
                500                 505                 510

Ser Ala Val Pro Ile Asp Trp Val Pro Thr Gly Arg Thr Thr Trp Ser
                515                 520                 525

Ile His Ala Thr Gly Glu Trp Met Ser Ser Asp Asp Met Leu Glu Val
            530                 535                 540

Trp Asn Lys Val Trp Ile Gln Asp Asn Pro His Val Lys Asp Lys Thr
545                 550                 555                 560

Pro Ile Phe Ala Trp Arg Asp Val Pro Tyr Ile Gln Lys Gly Gln Asp
                565                 570                 575

Arg Ala Cys Gly Ser Leu Val Gly Thr Ser Leu Arg Ala Ser Trp Ala
                580                 585                 590

Glu Ser Ile Met Thr Ser Val His Arg Val Arg Met Leu Ile Gly Asn
            595                 600                 605

Glu Arg Tyr Val Asn Tyr Met Glu Ser Met Asp Arg Tyr Ala Thr Gln
610                 615                 620

Arg Cys Ser Ala Tyr Gly Glu Leu Leu
625                 630

<210> SEQ ID NO 25
<211> LENGTH: 631
<212> TYPE: PRT
<213> ORGANISM: Flavivirus sp.
<220> FEATURE:
<221> NAME/KEY: misc_feature
<223> OTHER INFORMATION: Langat

<400> SEQUENCE: 25

Val Lys Glu Lys Asp Val Met Glu Arg Ile Gln Ala Leu Lys Asp Gln
1               5                   10                  15

Tyr Cys Asp Thr Trp His Glu Asp His Glu His Pro Tyr Arg Thr Trp
                20                  25                  30

Gln Tyr Trp Gly Ser Tyr Lys Thr Ala Ala Thr Gly Ser Ser Ala Ser
            35                  40                  45

Leu Leu Asn Gly Val Val Lys Leu Leu Ser Trp Pro Trp Asn Ala Arg
        50                  55                  60

Glu Asp Val Val Arg Met Ala Met Thr Asp Thr Thr Ala Phe Gly Gln
65                  70                  75                  80

Gln Arg Val Phe Lys Asp Lys Val Asp Thr Lys Ala Gln Glu Pro Gln
                85                  90                  95

Pro Gly Thr Lys Ile Ile Met Arg Ala Val Asn Asp Trp Leu Leu Glu
                100                 105                 110

Arg Leu Val Lys Lys Ser Arg Pro Arg Met Cys Ser Arg Glu Glu Phe
            115                 120                 125

Ile Ala Lys Val Arg Ser Asn Ala Ala Leu Gly Ala Trp Ser Asp Glu
        130                 135                 140

Gln Asn Lys Trp Lys Ser Ala Arg Glu Ala Val Glu Asp Pro Glu Phe
145                 150                 155                 160

Trp Ser Leu Val Glu Ala Glu Arg Glu Arg His Leu Gln Gly Arg Cys
                165                 170                 175

Ala His Cys Val Tyr Asn Met Met Gly Lys Arg Glu Lys Lys Leu Gly
```

```
                180             185             190
Glu Phe Gly Val Ala Lys Gly Ser Arg Ala Ile Trp Tyr Met Trp Leu
                195                 200                 205
Gly Ser Arg Phe Leu Glu Phe Glu Ala Leu Gly Phe Leu Asn Glu Asp
                210                 215                 220
His Trp Ala Ser Arg Ala Ser Ser Gly Ala Gly Val Glu Gly Ile Ser
225                 230                 235                 240
Leu Asn Tyr Leu Gly Trp His Leu Lys Lys Leu Ala Ser Leu Ser Gly
                245                 250                 255
Gly Leu Phe Tyr Ala Asp Asp Thr Ala Gly Trp Asp Thr Arg Ile Thr
                260                 265                 270
Asn Ala Asp Leu Asp Asp Glu Glu Gln Ile Leu Arg Tyr Met Asp Gly
                275                 280                 285
Asp His Lys Lys Leu Ala Ala Thr Val Leu Arg Lys Ala Tyr His Ala
                290                 295                 300
Lys Val Arg Val Ala Arg Pro Ser Arg Glu Gly Gly Cys Val Met
305                 310                 315                 320
Asp Ile Ile Thr Arg Arg Asp Gln Arg Gly Ser Gly Gln Val Val Thr
                325                 330                 335
Tyr Ala Leu Asn Thr Ile Thr Asn Ile Lys Val Gln Leu Val Arg Met
                340                 345                 350
Met Glu Gly Glu Gly Val Ile Glu Val Ala Asp Ser His Asn Pro Arg
                355                 360                 365
Leu Leu Arg Val Glu Lys Trp Leu Glu His Gly Glu Glu Arg Leu
                370                 375                 380
Ser Arg Met Leu Val Ser Gly Asp Asp Cys Val Val Arg Pro Val Asp
385                 390                 395                 400
Asp Arg Phe Ser Lys Ala Leu Tyr Phe Leu Asn Asp Met Ala Lys Thr
                405                 410                 415
Arg Lys Asp Thr Gly Glu Trp Glu Pro Ser Thr Gly Phe Ala Ser Trp
                420                 425                 430
Glu Glu Val Pro Phe Cys Ser His His Phe His Glu Leu Val Met Lys
                435                 440                 445
Asp Gly Arg Ala Leu Val Val Pro Cys Arg Asp Gln Asp Glu Leu Val
450                 455                 460
Gly Arg Ala Arg Val Ser Pro Gly Cys Gly Trp Ser Val Arg Glu Thr
465                 470                 475                 480
Ala Cys Leu Ser Lys Ala Tyr Gly Gln Met Trp Leu Leu Ser Tyr Phe
                485                 490                 495
His Arg Arg Asp Leu Arg Thr Leu Gly Phe Ala Ile Cys Ser Ala Val
                500                 505                 510
Pro Val Asp Trp Val Pro Thr Gly Arg Thr Thr Trp Ser Ile His Ala
                515                 520                 525
Ser Gly Ala Trp Met Thr Thr Glu Asp Met Leu Glu Val Trp Asn Arg
                530                 535                 540
Val Trp Ile Tyr Asp Asn Pro Phe Met Glu Asp Lys Thr Arg Val Asp
545                 550                 555                 560
Glu Trp Arg Asp Thr Pro Tyr Leu Pro Lys Ser Gln Asp Ile Leu Cys
                565                 570                 575
Ser Ser Leu Val Gly Arg Gly Glu Arg Ala Glu Trp Ala Lys Asn Ile
                580                 585                 590
Trp Gly Ala Val Glu Lys Val Arg Arg Met Ile Gly Pro Glu His Tyr
                595                 600                 605
```

Arg Asp Tyr Leu Ser Ser Met Asp Arg His Asp Leu His Trp Glu Leu
610                 615                 620

Lys Leu Glu Ser Ser Ile Phe
625                 630

<210> SEQ ID NO 26
<211> LENGTH: 631
<212> TYPE: PRT
<213> ORGANISM: Flavivirus sp.
<220> FEATURE:
<221> NAME/KEY: misc_feature
<223> OTHER INFORMATION: Powassan

<400> SEQUENCE: 26

Val Lys Pro Arg Asp Val Ala Glu Arg Ile Gly Ala Leu Arg Glu Gln
1               5                   10                  15

Tyr Ser Glu Ser Trp His Glu Asp Lys Glu His Pro Tyr Arg Thr Trp
                20                  25                  30

Gln Tyr Trp Gly Ser Tyr Arg Thr Pro Ala Thr Gly Ser Ala Ala Ser
            35                  40                  45

Leu Ile Asn Gly Val Val Lys Leu Leu Ser Trp Pro Trp Asn Ala Arg
50                  55                  60

Glu Asp Val Thr Arg Met Ala Met Thr Asp Thr Thr Ala Phe Gly Gln
65                  70                  75                  80

Gln Arg Val Phe Lys Glu Lys Val Asp Thr Lys Ala Gln Glu Pro Gln
                85                  90                  95

Pro Gly Thr Arg Val Ile Met Arg Ala Val Ser Asp Trp Leu Leu Glu
            100                 105                 110

His Leu Ser Arg Arg Ala Lys Val Arg Met Cys Thr Lys Asp Glu Phe
        115                 120                 125

Ile Ala Lys Val Arg Ser Asn Ala Ala Leu Gly Ala Trp Ser Asp Glu
130                 135                 140

Gln Asn Lys Trp Ser Ser Ala Lys Glu Ala Val Glu Asp Pro Glu Phe
145                 150                 155                 160

Trp Lys Leu Val Asp Glu Glu Arg Ser Arg His Leu Lys Gly Gln Cys
                165                 170                 175

Arg His Cys Val Tyr Asn Met Met Gly Lys Arg Glu Lys Lys Leu Gly
            180                 185                 190

Glu Phe Gly Val Ala Lys Gly Ser Arg Ala Ile Trp Tyr Met Trp Leu
        195                 200                 205

Gly Ser Arg Phe Leu Glu Phe Glu Val Leu Gly Phe Leu Asn Glu Glu
210                 215                 220

His Trp Ala Ser Arg Glu Val Ser Gly Ala Gly Val Glu Gly Thr Ser
225                 230                 235                 240

Leu Asn Tyr Leu Gly Trp Leu Leu Arg Glu Leu Gly Met Lys Asp Gly
                245                 250                 255

Gly Lys Leu Tyr Ala Asp Asp Thr Ala Gly Trp Asp Thr Arg Ile Thr
            260                 265                 270

Asn Ala Asp Leu Glu Asp Glu Glu Gln Ile Leu Arg Tyr Met Glu Gly
        275                 280                 285

Glu His His Val Leu Ala Lys Thr Ile Leu Glu Lys Ala Tyr His Ala
290                 295                 300

Lys Val Val Lys Val Ala Arg Pro Ser Pro Gln Gly Gly Cys Val Met
305                 310                 315                 320

Asp Val Ile Thr Arg Arg Asp Gln Arg Gly Ser Gly Gln Val Val Thr
                325                 330                 335

```
Tyr Ala Leu Asn Thr Ile Thr Asn Met Lys Val Gln Leu Ile Arg Met
                340                 345                 350

Met Glu Gly Glu Gly Val Ile Gly Pro Ala Asp Ser Gln Asp Pro Arg
            355                 360                 365

Leu Lys Arg Val Glu Thr Trp Leu Lys Glu Tyr Gly Val Glu Arg Leu
        370                 375                 380

Gly Arg Met Leu Val Ser Gly Asp Cys Val Val Lys Pro Ile Asp
385                 390                 395                 400

Asp Arg Phe Gly Lys Ala Leu Tyr Phe Leu Asn Met Asp Lys Val
                405                 410                 415

Arg Lys Asp Val Gly Glu Trp Glu Pro Ser Met Gly Leu Thr Glu Trp
            420                 425                 430

Glu Glu Val Pro Phe Cys Ser His His Phe His Glu Leu Val Met Lys
        435                 440                 445

Asp Gly Arg Ser Leu Ile Val Pro Cys Arg Asp Gln Asp Glu Leu Val
    450                 455                 460

Gly Arg Ala Arg Val Ser Pro Gly Cys Gly Trp Ser Val Arg Glu Thr
465                 470                 475                 480

Ala Cys Leu Ser Lys Ala Tyr Gly His Met Trp Leu Leu Asn Tyr Phe
                485                 490                 495

His Arg Arg Asp Leu Arg Thr Leu Gly Phe Ala Ile Cys Ser Ala Val
            500                 505                 510

Pro Val Ser Trp Val Pro Met Gly Arg Thr Thr Trp Ser Ile His Ala
        515                 520                 525

Ser Gly Glu Trp Met Thr Thr Glu Asp Met Leu Arg Ile Trp Asn Lys
    530                 535                 540

Val Trp Ile Leu Asp Asn Pro His Met Glu Asp Lys Thr Gln Val Asp
545                 550                 555                 560

Glu Trp Arg Asp Ile Pro Tyr Leu Pro Lys Thr Gln Asp Leu Val Cys
                565                 570                 575

Ser Ser Leu Val Gly Arg Lys Glu Arg Ala Glu Trp Ala Lys Asn Ile
            580                 585                 590

Trp Gly Ser Val Glu Lys Val Arg Lys Leu Ile Gly Pro Glu Asp Tyr
        595                 600                 605

Arg Asp Tyr Leu Ser Ser Met Asp Arg His Asp Leu His Trp Glu Leu
    610                 615                 620

Lys Leu Glu Ser Ser Ile Ile
625                 630

<210> SEQ ID NO 27
<211> LENGTH: 631
<212> TYPE: PRT
<213> ORGANISM: Flavivirus sp.
<220> FEATURE:
<221> NAME/KEY: misc_feature
<223> OTHER INFORMATION: Tick-borne Encephalitis

<400> SEQUENCE: 27

Val Lys Glu Lys Asp Val Gln Glu Arg Ile Ser Ala Leu Arg Glu Gln
1               5                   10                  15

Tyr Gly Glu Thr Trp His Met Asp Arg Glu His Pro Tyr Arg Thr Trp
            20                  25                  30

Gln Tyr Trp Gly Ser Tyr Arg Thr Ala Pro Thr Gly Ser Ala Ala Ser
        35                  40                  45

Leu Ile Asn Gly Val Val Lys Leu Leu Ser Trp Pro Trp Asn Ala Arg
    50                  55                  60
```

-continued

```
Glu Asp Val Val Arg Met Ala Met Thr Asp Thr Thr Ala Phe Gly Gln
 65                  70                  75                  80

Gln Arg Val Phe Lys Glu Lys Val Asp Thr Lys Ala Gln Glu Pro Gln
                 85                  90                  95

Pro Gly Thr Lys Val Ile Met Arg Ala Val Asn Asp Trp Ile Leu Glu
            100                 105                 110

Arg Leu Ala Arg Lys Ser Lys Pro Arg Met Cys Ser Arg Glu Glu Phe
        115                 120                 125

Ile Ala Lys Val Lys Ser Asn Ala Ala Leu Gly Ala Trp Ser Asp Glu
130                 135                 140

Gln Asn Arg Trp Ser Ser Ala Lys Glu Ala Val Glu Asp Pro Ala Phe
145                 150                 155                 160

Trp Gln Leu Val Asp Glu Glu Arg Glu Arg His Leu Ala Gly Arg Cys
                165                 170                 175

Ala His Cys Val Tyr Asn Met Met Gly Lys Arg Glu Lys Lys Leu Gly
            180                 185                 190

Glu Phe Gly Val Ala Lys Gly Ser Arg Ala Ile Trp Tyr Met Trp Leu
        195                 200                 205

Gly Ser Arg Phe Leu Glu Phe Glu Ala Leu Gly Phe Leu Asn Glu Asp
210                 215                 220

His Trp Ala Ser Arg Gly Ser Ser Gly Ser Gly Val Glu Gly Ile Ser
225                 230                 235                 240

Leu Asn Tyr Leu Gly Trp His Leu Lys Gly Leu Ser Thr Leu Glu Gly
                245                 250                 255

Gly Leu Phe Tyr Ala Asp Asp Thr Ala Gly Trp Asp Thr Lys Val Thr
            260                 265                 270

Asn Ala Asp Leu Glu Asp Glu Glu Gln Leu Leu Arg Tyr Met Glu Gly
        275                 280                 285

Glu His Lys Gln Leu Ala Ala Thr Ile Met Gln Lys Ala Tyr His Ala
290                 295                 300

Lys Val Val Lys Val Ala Arg Pro Ser Arg Asp Gly Gly Cys Ile Met
305                 310                 315                 320

Asp Val Ile Thr Arg Arg Asp Gln Arg Gly Ser Gly Gln Val Val Thr
                325                 330                 335

Tyr Ala Leu Asn Thr Leu Thr Asn Ile Lys Val Gln Leu Ile Arg Met
            340                 345                 350

Met Glu Gly Glu Gly Val Ile Glu Ala Ser Asp Ala His Asn Pro Arg
        355                 360                 365

Leu Leu Arg Val Glu Arg Trp Leu Arg Asp His Gly Glu Glu Arg Leu
370                 375                 380

Gly Arg Met Leu Val Ser Gly Asp Asp Cys Val Val Arg Pro Val Asp
385                 390                 395                 400

Asp Arg Phe Ser Gly Ala Leu Tyr Phe Leu Asn Asp Met Ala Lys Thr
                405                 410                 415

Arg Lys Asp Ile Gly Glu Trp Glu His Ser Val Gly Phe Ser Asn Trp
            420                 425                 430

Glu Glu Val Pro Phe Cys Ser His His Phe His Glu Leu Val Met Lys
        435                 440                 445

Asp Gly Arg Ala Leu Ile Val Pro Cys Arg Asp Gln Asp Glu Leu Val
450                 455                 460

Gly Arg Ala Arg Val Ser Pro Gly Cys Gly Trp Ser Val Arg Glu Thr
465                 470                 475                 480

Ala Cys Leu Ser Lys Ala Tyr Gly Gln Met Trp Leu Leu Ser Tyr Phe
                485                 490                 495
```

His Arg Arg Asp Leu Arg Thr Leu Gly Leu Ala Ile Cys Ser Ala Val
            500                 505                 510

Pro Val Asp Trp Val Pro Thr Gly Arg Thr Thr Trp Ser Ile His Ala
            515                 520                 525

Ser Gly Ala Trp Met Thr Thr Glu Asp Met Leu Asp Val Trp Asn Arg
            530                 535                 540

Val Trp Ile Leu Asp Asn Pro Phe Met His Ser Lys Glu Lys Ile Ala
545                 550                 555                 560

Glu Trp Arg Asp Val Pro Tyr Leu Pro Lys Ser His Asp Met Leu Cys
                565                 570                 575

Ser Ser Leu Val Gly Arg Lys Glu Arg Ala Glu Trp Ala Lys Asn Ile
            580                 585                 590

Trp Gly Ala Val Glu Lys Val Arg Lys Met Ile Gly Gln Glu Lys Phe
            595                 600                 605

Lys Asp Tyr Leu Ser Cys Met Asp Arg His Asp Leu His Trp Glu Leu
610                 615                 620

Lys Leu Glu Ser Ser Ile Ile
625                 630

<210> SEQ ID NO 28
<211> LENGTH: 631
<212> TYPE: PRT
<213> ORGANISM: Flavivirus sp.
<220> FEATURE:
<221> NAME/KEY: misc_feature
<223> OTHER INFORMATION: LoupingIll

<400> SEQUENCE: 28

Val Lys Glu Gln Asp Val Gln Glu Arg Ile Arg Ala Leu Arg Lys Gln
1               5                   10                  15

Tyr Ser Glu Thr Trp His Met Asp Glu Glu His Pro Tyr Arg Thr Trp
            20                  25                  30

Gln Tyr Trp Gly Thr Ser Arg Thr Ala Pro Thr Gly Ser Ala Ala Ser
            35                  40                  45

Leu Ile Asn Gly Val Val Lys Leu Leu Ser Trp Pro Trp Asn Ala Arg
        50                  55                  60

Glu Asp Val Val Arg Met Ala Met Thr Asp Thr Thr Ala Phe Gly Gln
65                  70                  75                  80

Gln Arg Val Phe Lys Glu Lys Val Asp Thr Lys Ala Gln Glu Pro Gln
                85                  90                  95

Pro Gly Thr Arg Val Ile Thr Arg Ala Val Asn Asp Trp Ile Leu Glu
            100                 105                 110

Arg Leu Ala Gln Lys Ser Lys Pro Arg Met Cys Ser Arg Glu Glu Phe
        115                 120                 125

Ile Ala Lys Val Arg Ser Asn Ala Ala Leu Gly Ala Trp Ser Asp Glu
130                 135                 140

Gln Asn Arg Trp Ala Ser Ala Arg Glu Ala Val Val Pro Ala Phe
145                 150                 155                 160

Trp Ala Leu Val Asp Glu Val Arg Glu His Leu Val Gly Trp Cys
                165                 170                 175

Ala His Cys Val Tyr Ile Met Met Gly Met Arg Glu Lys Lys Leu Gly
            180                 185                 190

Glu Phe Gly Val Ala Lys Gly Ser Arg Ala Ile Trp Tyr Met Trp Leu
        195                 200                 205

Gly Ser Arg Phe Leu Glu Phe Glu Ala Leu Gly Phe Leu Asn Lys Asp
    210                 215                 220

```
His Trp Ala Ser Arg Glu Ser Ser Gly Gly Val Glu Gly Ile Ser
225                 230                 235                 240

Leu Asn Tyr Leu Gly Trp His Leu Lys Lys Leu Thr Thr Leu Asn Gly
            245                 250                 255

Gly Leu Phe Tyr Ala Asp Asp Thr Ala Gly Trp Asp Thr Lys Gly Thr
                260                 265                 270

Asn Ser Asp Pro Glu Asp Glu Glu Gln Ile Leu Arg Tyr Met Glu Gly
            275                 280                 285

Glu His Lys Gln Leu Ala Thr Thr Ile Met Gln Lys Ala Tyr His Ala
        290                 295                 300

Lys Val Val Lys Val Ala Arg Pro Ser Arg Asp Gly Gly Cys Ile Met
305                 310                 315                 320

Asp Val Ile Thr Arg Arg Asp Gln Arg Gly Ser Gly Gln Val Val Thr
                325                 330                 335

Tyr Ala Leu Asn Thr Leu Thr Asn Ile Lys Val Gln Ser Thr Arg Met
                340                 345                 350

Met Glu Gly Glu Gly Val Ile Glu Ala Glu Asp Ala His Asn Pro Arg
            355                 360                 365

Leu Leu Arg Val Glu Arg Trp Leu Lys Glu His Gly Glu Glu Arg Leu
370                 375                 380

Gly Arg Met Leu Val Ser Gly Asp Asp Cys Val Val Arg Pro Ile Asp
385                 390                 395                 400

Asp Arg Phe Gly Lys Ala Leu Tyr Phe Leu Asn Asp Met Ala Lys Thr
                405                 410                 415

Arg Lys Asp Met Gly Glu Trp Glu Pro Ser Ala Gly Phe Ser Ser Trp
                420                 425                 430

Glu Glu Val Pro Phe Cys Ser His His Phe His Glu Leu Val Met Lys
                435                 440                 445

Asp Gly Arg Thr Leu Val Val Pro Cys Arg Asp Gln Asp Glu Leu Val
450                 455                 460

Gly Arg Ala Arg Val Ser Pro Gly Cys Gly Trp Ser Val Arg Glu Thr
465                 470                 475                 480

Ala Cys Leu Ser Lys Ala Tyr Gly Gln Met Trp Leu Leu Ser Tyr Phe
                485                 490                 495

His Arg Arg Asp Leu Arg Thr Leu Gly Phe Ala Ile Ser Pro Ala Val
            500                 505                 510

Pro Val Asp Trp Val Pro Thr Gly Arg Thr Thr Trp Ser Ile His Ala
            515                 520                 525

Ser Gly Ala Trp Met Thr Thr Glu Asp Met Leu Asp Val Trp Asn Arg
    530                 535                 540

Val Trp Ile Leu Asp Asn Pro Phe Met Gln Asn Lys Glu Arg Ile Met
545                 550                 555                 560

Glu Trp Arg Asp Val Pro Tyr Leu Pro Lys Thr Gln Asp Met Ile Cys
                565                 570                 575

Ser Ser Leu Val Gly Arg Lys Glu Arg Ala Glu Trp Ala Lys Asn Ile
            580                 585                 590

Trp Gly Ala Val Glu Lys Val Arg Lys Met Ile Gly Pro Glu Arg Phe
    595                 600                 605

Lys Asp Tyr Leu Ser Cys Met Asp Arg His Asp Leu His Trp Glu Leu
    610                 615                 620

Lys Leu Glu Ser Ser Ile Ile
625                 630
```

<210> SEQ ID NO 29
<211> LENGTH: 625
<212> TYPE: PRT
<213> ORGANISM: Flavivirus sp.
<220> FEATURE:
<221> NAME/KEY: misc_feature
<223> OTHER INFORMATION: Modoc

<400> SEQUENCE: 29

```
Val Pro Glu Glu Val Gln Met Arg Val Asp Lys Ile Lys Ala Glu
1               5                  10                  15

Lys Ser Gly Thr Trp Cys Phe Asp Ser Asn His Pro Tyr Arg Thr Trp
            20                  25                  30

Asn Tyr His Gly Ser Tyr Arg Val Arg Asp Val Gly Thr Arg Ala Ser
                35                  40                  45

Ala Val Asn His Val Val Lys Leu Leu Ser Trp Pro Trp Gly Lys Met
    50                  55                  60

Glu Lys Val Leu Ala Met Ser Met Thr Asp Thr Thr Ala Phe Gly Gln
65                  70                  75                  80

Gln Arg Val Phe Lys Gln Lys Val Asp Thr Lys Ala Pro Glu Pro Asn
                85                  90                  95

Ile Gln Val Lys Lys Val Met Arg Lys Val Phe Lys Trp Leu Ile Glu
            100                 105                 110

Arg Ile Lys Thr Lys Gly Gly Lys Val Arg Thr Cys Thr Lys Glu Glu
        115                 120                 125

Phe Ile Gln Lys Val Arg Ser His Ala Ala Ile Gly Ala Trp Ser Ser
130                 135                 140

Asp Met Glu Gly Trp Ser Ser Ala Val Glu Ala Val Asp Asp Pro Arg
145                 150                 155                 160

Phe Trp Asn Met Val Gln Lys Glu Arg Asp Leu His Leu Gln Gly Lys
                165                 170                 175

Cys Glu Met Cys Val Tyr Asn Leu Met Gly Lys Ser Glu Lys Lys Pro
            180                 185                 190

Gly Asp Phe Gly Val Ala Lys Gly Ser Arg Thr Ile Trp Tyr Met Trp
        195                 200                 205

Leu Gly Ser Arg Phe Leu Glu Phe Glu Ser Phe Gly Phe Leu Asn Glu
    210                 215                 220

Glu His Trp Ala Ser Arg Glu Leu Ser Gly Gly Val Glu Gly Ile
225                 230                 235                 240

Pro Leu Asn Tyr Leu Gly Tyr His Leu Arg Glu Met Ala Gln Lys Pro
                245                 250                 255

Gly Val Leu Tyr Ala Asp Asp Thr Ala Gly Trp Asp Thr Arg Ile Thr
            260                 265                 270

Met Ala Asp Leu Glu Asp Glu Gly Met Leu Leu Asp Met Met Ser Gly
        275                 280                 285

Glu His Lys Lys Leu Ala Ser Ala Leu Phe Ser Lys Ala Tyr Lys Val
    290                 295                 300

Lys Val Ala Leu Cys Pro Arg Pro Gly Pro Lys Gly Gly Thr Leu Met
305                 310                 315                 320

Asp Val Ile Ser Arg Thr Asp Gln Arg Gly Ser Gly Gln Val Val Thr
                325                 330                 335

Tyr Ala Leu Asn Thr Leu Thr Asn Ile Lys Val Gln Leu Ile Arg Met
            340                 345                 350

Ala Glu Ala Glu Gly Val Leu Gly Ala Thr Phe Glu Asp Phe Gly Ile
        355                 360                 365

Asp Arg Trp Leu Gln Glu His Gly Glu Asp Arg Val Glu Arg Met Leu
```

```
               370                 375                 380
Val Ser Gly Asp Asp Cys Val Asn Ala Ile Asp Glu Arg Phe Gly
385                 390                 395                 400

Ser Ser Leu Asn Trp Leu Asn Ala Met Glu Lys Val Arg Lys Asp Ile
                405                 410                 415

Asp Leu Trp Lys Pro Ser Pro Ser Phe Arg Asn Trp Glu Arg Val Glu
                420                 425                 430

Phe Cys Ser Asn His Phe His Glu Met Thr Met Lys Asp Gly Arg Val
                435                 440                 445

Ile Val Ala Pro Cys Arg Gly Gln Thr Glu Leu Ile Ala Arg Gly Thr
                450                 455                 460

Val Asn Gln Gly Gly Cys Val Gly Val Glu Ser Thr Gly Cys Leu Ala
465                 470                 475                 480

Lys Ala Tyr Ala Gln Met Trp Leu Leu Leu Tyr Phe His Arg Arg Asp
                485                 490                 495

Leu Arg Thr Leu Ala Leu Ala Val Met Ser Ala Val Pro Ser Asn Trp
                500                 505                 510

Ile Pro Thr Gly Arg Thr Thr Trp Ser Leu Met Val Lys Gly Glu Trp
                515                 520                 525

Met Thr Asp Glu Asp Met Leu Ala Val Trp Asn Arg Val Trp Ile Glu
530                 535                 540

Asp Asn Pro Phe Met Glu Asp Lys Arg Glu Val Arg Trp Ser Glu
545                 550                 555                 560

Val Pro Tyr Leu Pro Arg Asn Gln Asp Lys Ser Cys Gly Ser Leu Ile
                565                 570                 575

Gly Thr Thr Ala Arg Ala Glu Trp Ala Lys Leu Leu Pro Gly Ala Val
                580                 585                 590

Glu Lys Val Arg Asn Ile Phe Gly Lys Gln Arg Phe Arg Asn Tyr Leu
                595                 600                 605

Arg Asn Met Gly Arg Tyr Glu Ser Gln Glu Ala Pro Phe Ser Met
    610                 615                 620

Tyr
625

<210> SEQ ID NO 30
<211> LENGTH: 624
<212> TYPE: PRT
<213> ORGANISM: Flavivirus sp.
<220> FEATURE:
<221> NAME/KEY: misc_feature
<223> OTHER INFORMATION: Rio Bravo

<400> SEQUENCE: 30

Ala Asp Lys Ser Leu Ile Ala Asp Arg Ile Thr Ile Ile Gln Asn Glu
1               5                   10                  15

Asn Lys Ala Ser Trp His Gln Asp Pro Asn Gln Pro Tyr Arg Thr Trp
                20                  25                  30

Thr Tyr His Gly Ser Tyr Ser Ile Arg Asp Val Gly Thr Ser Ala Ser
            35                  40                  45

Ala Pro Asn His Val Val Lys Leu Leu Ala Trp Pro Trp Leu Lys Ile
        50                  55                  60

Glu Lys Val Val Leu Met Ala Met Thr Asp Thr Ala Phe Gly Gln
65                  70                  75                  80

Gln Arg Val Phe Lys Glu Lys Val Asp Thr Lys Ala Pro Glu Pro Pro
                85                  90                  95

Lys Glu Val Lys Lys Val Met Arg Leu Val Phe Arg Trp Leu Leu Asn
```

```
                100              105                 110
His Ile Lys Ser Lys Gly Ala Val Val Arg Arg Cys Thr Lys Glu Glu
            115                 120             125

Phe Ile Asn Lys Val Asn Ser Asn Ala Ser Ile Gly Ala Tyr Leu Arg
130             135             140

Glu Met Gly Glu Trp Ser Ser Ala Lys Glu Ala Val Ser Asp Pro Lys
145                 150             155                 160

Phe Trp Asn Met Val Asp Lys Glu Arg Gln Leu His Leu Lys Gly Lys
                165             170             175

Cys His Asn Cys Val Tyr Asn Leu Met Gly Lys Arg Glu Lys Lys Pro
            180             185             190

Gly Glu Phe Gly Val Ala Lys Gly Ser Arg Thr Ile Trp Tyr Met Trp
            195             200             205

Leu Gly Ser Arg Phe Leu Glu Phe Glu Ala Leu Gly Phe Leu Asn Glu
            210             215             220

Glu Arg Trp Ala Ser Arg Asp Ile Ser Gly Gly Gly Val Glu Gly Ile
225             230             235                 240

Gly Ile Asn Tyr Leu Gly Tyr His Leu Glu Lys Met Ala Arg Lys Val
                245             250             255

Gly Val Leu Tyr Ala Asp Asp Thr Ala Gly Trp Asp Thr Arg Val Thr
            260             265             270

Gln Ala Asp Leu Glu Asp Glu Arg Glu Leu Leu His Phe Met Glu Gly
            275             280             285

Glu His Lys Arg Leu Ala Glu Ala Ile Phe Lys Leu Thr Tyr Glu Asn
            290             295             300

Lys Val Ala Leu Cys Pro Arg Pro Gly Ser Lys Gly Gly Thr Val Met
305             310             315                 320

Asp Val Ile Ser Arg Lys Asp Gln Arg Gly Ser Gly Gln Val Val Thr
                325             330             335

Tyr Ala Leu Asn Thr Leu Thr Asn Ile Lys Val Gln Leu Val Arg Met
                340             345             350

Ala Glu Ser Glu Gly Ile Leu Thr Pro Glu Leu Glu Asp Leu Gly Ile
            355             360             365

Glu Gln Trp Leu Lys Gln Asn Gly Glu Asp Arg Leu Ser Arg Leu Leu
            370             375             380

Val Ser Gly Asp Asp Cys Val Val Asn Ala Leu Asp Glu Arg Phe Gly
385             390             395                 400

Lys Ala Leu Thr Trp Leu Asn Thr Met Glu Lys Thr Arg Lys Asp Ile
                405             410             415

Glu Ala Trp Lys Pro Ser Arg Ala Tyr Arg Thr Trp Gln Glu Val Glu
            420             425             430

Phe Cys Ser His His Phe His Glu Leu Phe Leu Arg Asp Gly Arg Lys
            435             440             445

Leu Ile Val Pro Cys Arg Asp Gln His Glu Leu Val Gly Arg Ser Met
            450             455             460

Val Ser Gln Gly Gly Ser Ser Gly Val Ala Gly Thr Ala Cys Leu Ala
465             470             475             480

Lys Ala Tyr Ala Gln Met Trp Leu Met Ser Tyr Phe His Arg Arg Asp
                485             490             495

Leu Arg Thr Leu Gly Phe Ala Ile Met Ser Ser Val Pro Lys Asp Trp
            500             505             510

Phe Pro Thr Gly Arg Thr Thr Trp Ser Val His Ala Asn His Glu Trp
            515             520             525
```

-continued

| | | | | | | | | | | | | | | |
|---|---|---|---|---|---|---|---|---|---|---|---|---|---|---|
| Leu | Ser | Asn | Glu | Asn | Ile | Leu | Glu | Ile | Trp | Asn | Arg | Val | Trp | Ile | Glu |
| | 530 | | | | 535 | | | | | 540 | | | | | |
| Glu | Asn | Pro | Phe | Met | Glu | Asp | Lys | Thr | Thr | Val | Ala | Glu | Trp | Lys | Asn |
| 545 | | | | | 550 | | | | | 555 | | | | | 560 |
| Ile | Pro | Tyr | Leu | Gln | Arg | Asn | Gln | Asp | Leu | Ser | Cys | Ser | Ser | Leu | Ile |
| | | | | 565 | | | | | 570 | | | | | 575 | |
| Asp | Asn | Pro | Thr | Arg | Ala | Gln | Trp | Ala | Lys | Leu | Leu | Lys | Gly | Ala | Val |
| | | | 580 | | | | | 585 | | | | | 590 | | |
| Met | Lys | Val | Arg | Glu | Met | Ile | Gly | Arg | Glu | His | Tyr | Ser | Asp | Tyr | Leu |
| | | 595 | | | | | 600 | | | | | 605 | | | |
| Ser | Asn | Met | Gly | Arg | Tyr | Gln | Glu | Gly | Thr | Glu | Glu | Phe | His | Met | Trp |
| | 610 | | | | | 615 | | | | 620 | | | | | |

The invention claimed is:

1. An isolated and purified polypeptide from a *flavivirus*, consisting of 632 amino acids and wherein the full-length amino acid sequence of said polypeptide has at least 65% of identity with the SEQ ID NO: 20.

2. The isolated and purified polypeptide of claim 1, which is from West Nile virus.

3. The isolated and purified polypeptide of claim 1, which has polymerase activity.

4. An isolated and purified polypeptide consisting of the polymerase domain of the C-terminus of the NS5 polypeptide of a *flavivirus*, wherein said polypeptide has polymerase activity and wherein the full-length amino acid sequence of said polypeptide has at least 65% of identity with the SEQ ID NO: 20.

5. The isolated and purified polypeptide of claim 4, wherein the *flavivirus* is a West Nile virus.

6. The isolated and purified polypeptide of claim 1, wherein the full-length amino acid sequence of said polypeptide has at least 70% of identity with the SEQ ID NO: 20.

7. The isolated and purified polypeptide of claim 4, wherein the full-length amino acid sequence of said polypeptide has at least 70% of identity with the SEQ ID NO: 20.

* * * * *